(12) United States Patent
Jacobsen et al.

(10) Patent No.: US 12,268,453 B2
(45) Date of Patent: *Apr. 8, 2025

(54) NAVIGATION SYSTEM AND METHOD

(71) Applicant: Medtronic Navigation, Inc., Louisville, CO (US)

(72) Inventors: Brad Jacobsen, Erie, CO (US); Danail G. Danailov, Westminster, CO (US); Andrew Bzostek, Boulder, CO (US); Andrew Wald, Fort Worth, TX (US)

(73) Assignee: Medtronic Navigation, Inc., Lafayette, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,384

(22) Filed: Apr. 19, 2023

(65) Prior Publication Data
US 2023/0270509 A1    Aug. 31, 2023

Related U.S. Application Data

(60) Division of application No. 17/064,813, filed on Oct. 7, 2020, now Pat. No. 11,660,146, which is a (Continued)

(51) Int. Cl.
| | |
|---|---|
| A61B 5/00 | (2006.01) |
| A61B 5/06 | (2006.01) |
| A61B 34/20 | (2016.01) |
| G01D 5/20 | (2006.01) |
| G01R 33/02 | (2006.01) |

(Continued)

(52) U.S. Cl.
CPC .............. *A61B 34/20* (2016.02); *A61B 5/062* (2013.01); *G01D 5/204* (2013.01); *G01R 33/02* (2013.01); *H01F 27/28* (2013.01); *A61B 5/066* (2013.01); *A61B 2034/2051* (2016.02);
(Continued)

(58) Field of Classification Search
CPC .. G01B 7/003; G01B 7/004; A61B 2034/2051
See application file for complete search history.

(56) References Cited

U.S. PATENT DOCUMENTS

| | | |
|---|---|---|
| 3,996,510 A | 12/1976 | Guichard |
| 4,849,692 A | 7/1989 | Blood |

(Continued)

FOREIGN PATENT DOCUMENTS

| | | |
|---|---|---|
| CN | 101035484 A | 9/2007 |
| CN | 102188246 A | 9/2011 |

(Continued)

OTHER PUBLICATIONS

International Search Report and Written Opinion mailed Jul. 23, 2018 in corresponding/related International Application No. PCT/US2018/028598.

(Continued)

*Primary Examiner* — Rajeev P Siripurapu
(74) *Attorney, Agent, or Firm* — Harness, Dickey & Pierce, P.L.C.

(57) ABSTRACT

Disclosed is a localizer system. The localizer system may be incorporated into a navigation system for tracking a tracking device. Generally, the localizer may include a transmitting coil array and a field shaping assembly.

19 Claims, 15 Drawing Sheets

Related U.S. Application Data continuation of application No. 15/957,539, filed on Apr. 19, 2018, now Pat. No. 11,564,747.

(60) Provisional application No. 62/487,801, filed on Apr. 20, 2017.

(51) Int. Cl.
  *H01F 27/28* (2006.01)
  *A61B 90/00* (2016.01)

(52) U.S. Cl.
  CPC ....... *A61B 90/361* (2016.02); *A61B 2090/374* (2016.02); *A61B 2090/3762* (2016.02)

(56) References Cited

U.S. PATENT DOCUMENTS

| | | | |
|---|---|---|---|
| 4,890,083 A | 12/1989 | Trenkler et al. | |
| 5,359,149 A | 10/1994 | Seike et al. | |
| 5,593,939 A | 1/1997 | Saito et al. | |
| 5,640,170 A | 6/1997 | Anderson | |
| 5,752,513 A | 5/1998 | Acker et al. | |
| 5,912,820 A | 6/1999 | Kerzman et al. | |
| 6,246,231 B1 | 6/2001 | Ashe | |
| 6,493,573 B1 | 12/2002 | Martinelli et al. | |
| 6,528,991 B2 | 3/2003 | Ashe | |
| 6,784,660 B2 | 8/2004 | Ashe | |
| 7,697,972 B2 | 4/2010 | Verard et al. | |
| 8,380,289 B2 | 2/2013 | Zellers et al. | |
| 8,391,952 B2 | 3/2013 | Anderson | |
| 8,391,956 B2 | 3/2013 | Zellers et al. | |
| RE44,305 E | 6/2013 | Foley et al. | |
| 8,571,636 B2 | 10/2013 | Wu | |
| 8,611,986 B2 | 12/2013 | Wu | |
| 8,644,907 B2 | 2/2014 | Hartmann et al. | |
| 8,842,893 B2 | 9/2014 | Teichman et al. | |
| 10,765,483 B2 | 9/2020 | Jacobsen et al. | |
| 2003/0011359 A1 | 1/2003 | Ashe | |
| 2003/0173953 A1* | 9/2003 | Ashe | G01D 3/036 324/207.17 |
| 2004/0199072 A1 | 10/2004 | Sprouse et al. | |
| 2007/0197899 A1* | 8/2007 | Ritter | A61B 5/062 600/407 |
| 2010/0331671 A1 | 12/2010 | Martinelli et al. | |
| 2011/0224537 A1 | 9/2011 | Brunner | |
| 2014/0131087 A1 | 5/2014 | Staebler | |
| 2016/0081583 A1 | 3/2016 | Ikuma et al. | |
| 2018/0287411 A1 | 10/2018 | Lee et al. | |

FOREIGN PATENT DOCUMENTS

| | | |
|---|---|---|
| DE | 102009039600 B3 | 3/2011 |
| JP | 2002291113 A | 10/2002 |
| JP | 2007299923 A | 11/2007 |
| WO | 0130256 A1 | 5/2001 |
| WO | 0131466 A1 | 5/2001 |
| WO | 2004012646 A2 | 2/2004 |
| WO | 2012175846 A1 | 12/2012 |

OTHER PUBLICATIONS

International Preliminary Report on Patentabilty in corresponding/related International Application No. PCT/US2018/028598 mailed Oct. 31, 2019.
Bien. Electromagnetic tracking system with reduced distortion using quadratic excitation. International Journal of Computer Assisted Radiology and Surgery. ISSN 1861-6410. Int J CARS. DOI 10.1007/s11548-013-0925-4. Published 2013. (12 pages).
Chinese Office Action regarding Patent Application No. 201880025363.7, dated May 5, 2022.
Second Chinese Office Action regarding Patent Application No. 201880025363.7, dated Jul. 26, 2022.
European Patent Office Communication corresponding to European Application No. 187253489, Dated Nov. 24, 2022.
U.S. Appl. No. 15/957,582, filed Apr. 19, 2018, Bradley W. Jacobsen.
U.S. Appl. No. 17/064,813, filed Oct. 7, 2020, Bradley W. Jacobsen.
U.S. Appl. No. 62/487,801, filed Apr. 20, 2017, Bradley W. Jacobsen.

* cited by examiner

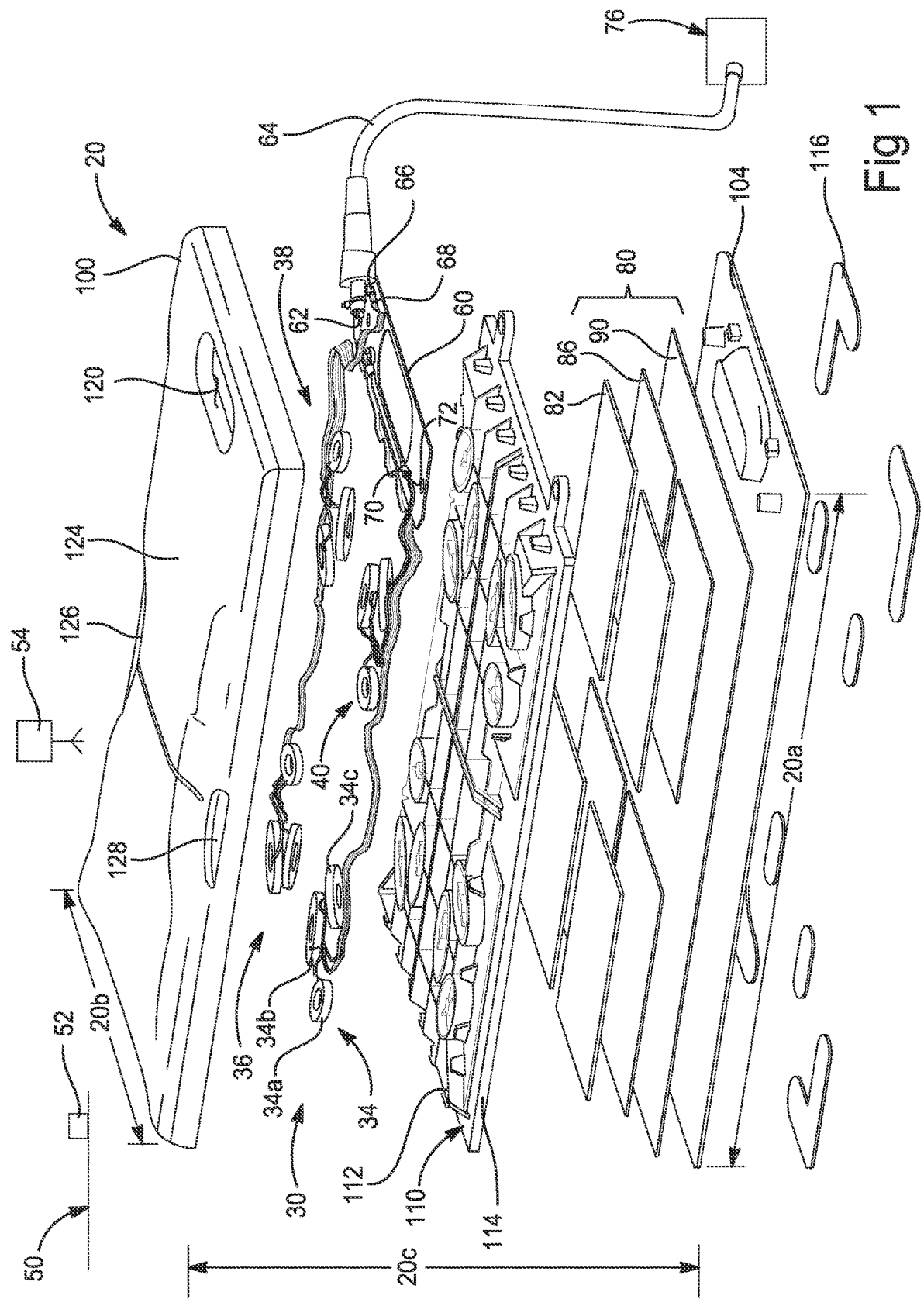

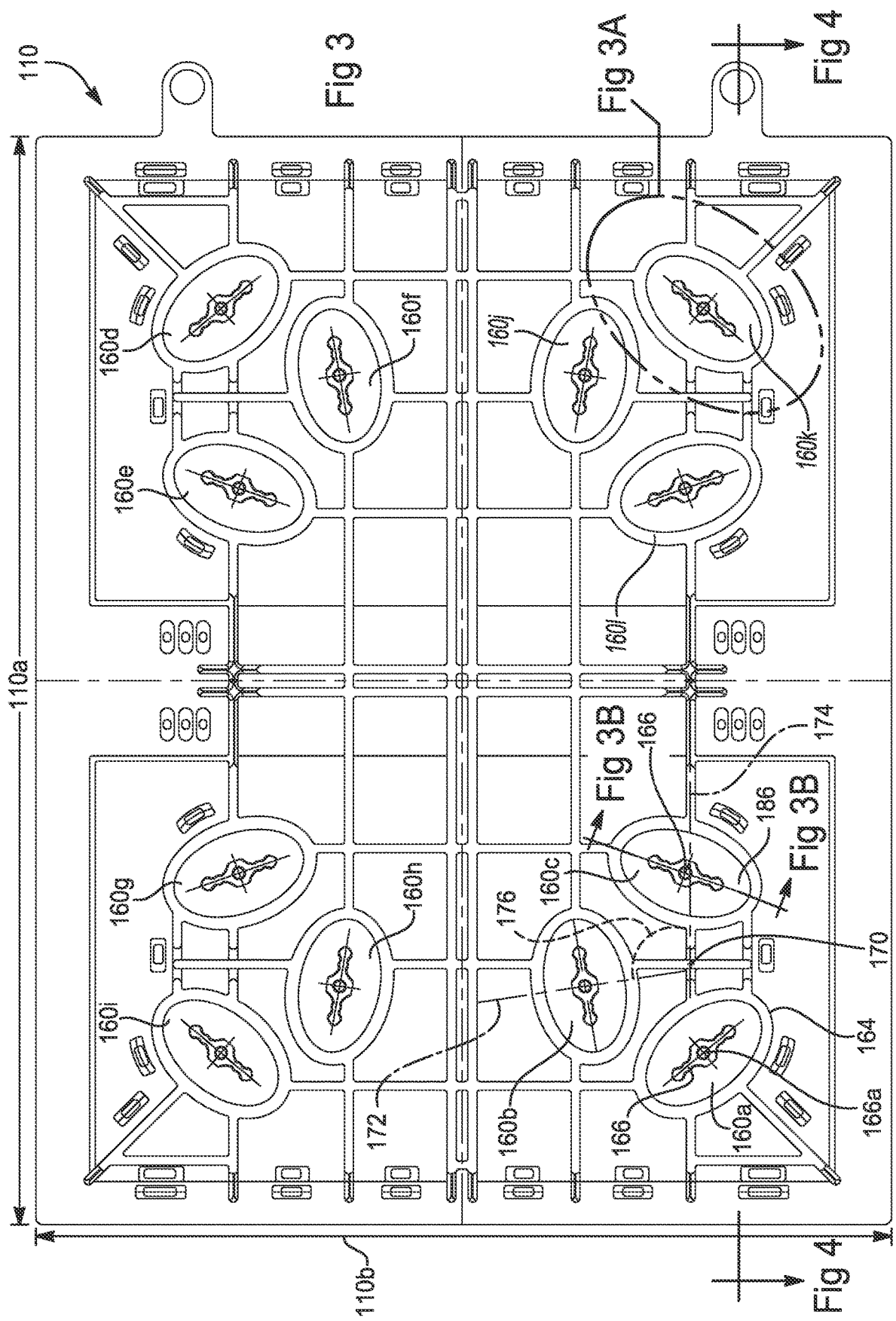

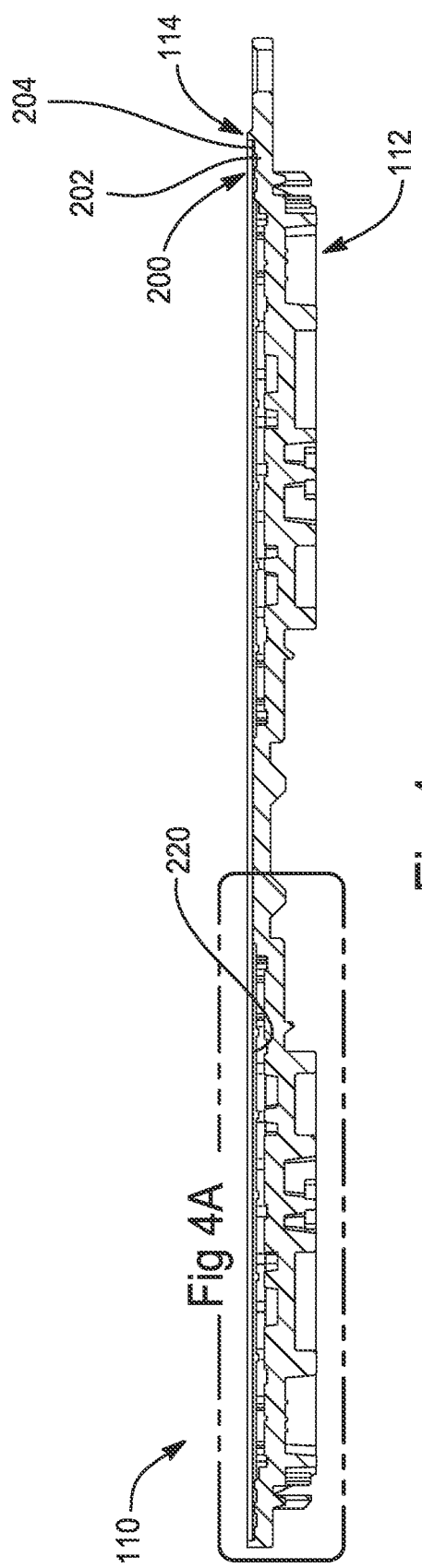
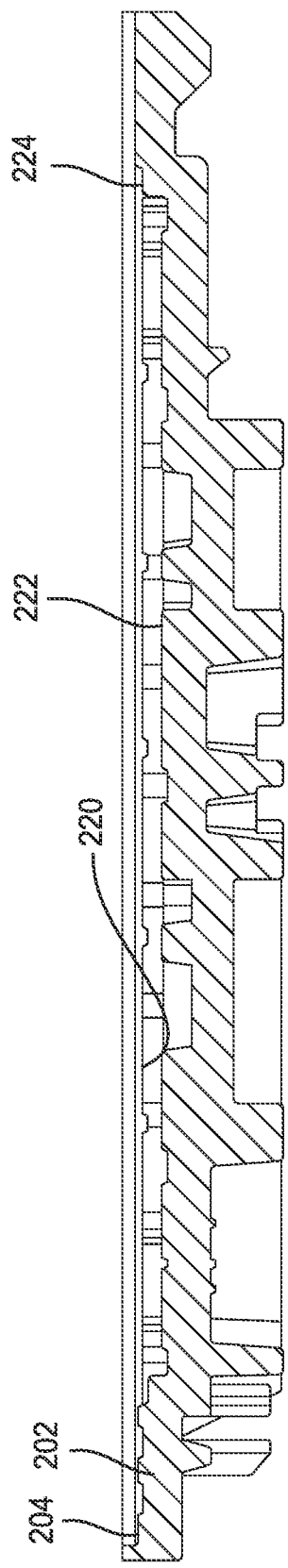
Fig 4
Fig 4A

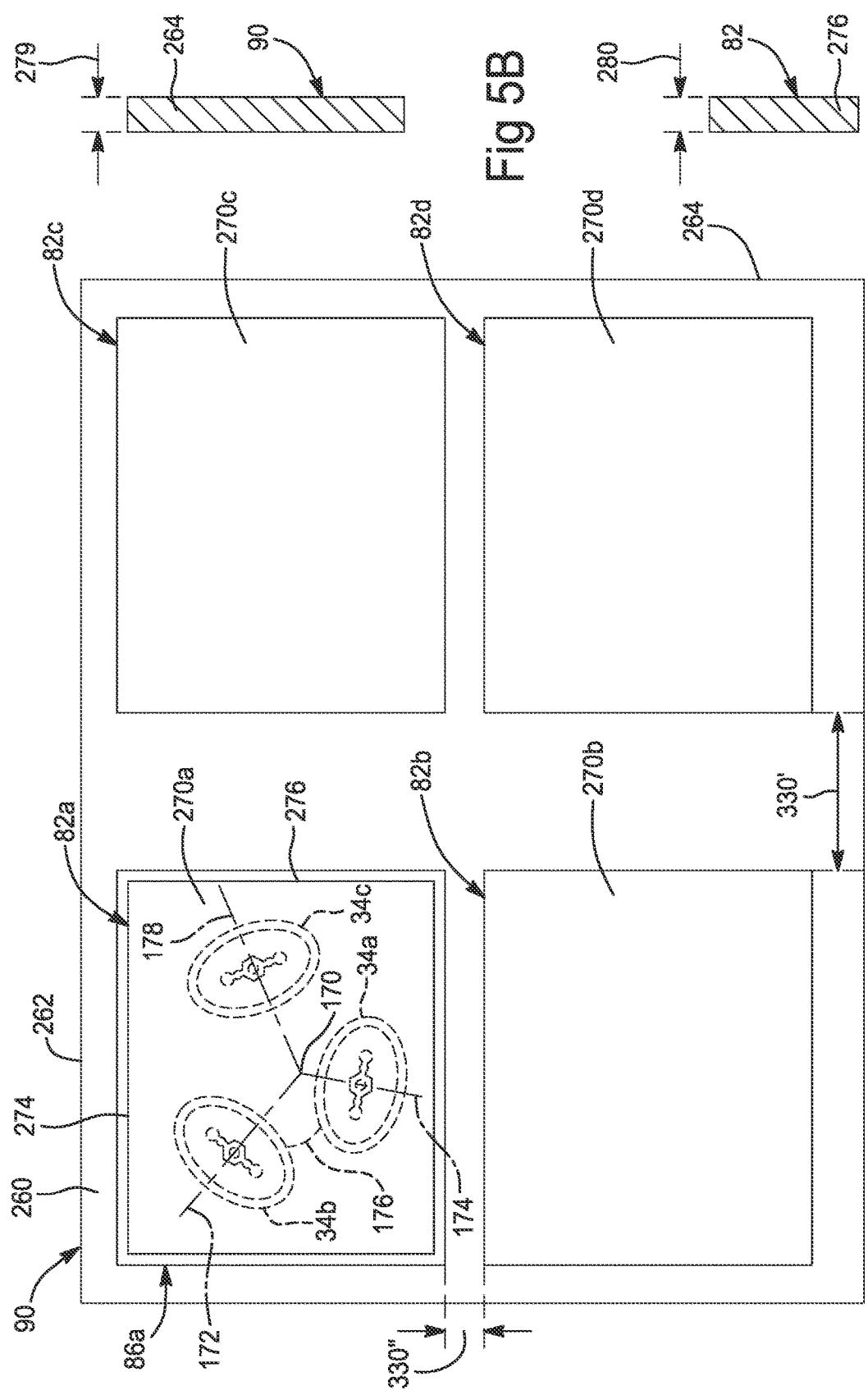

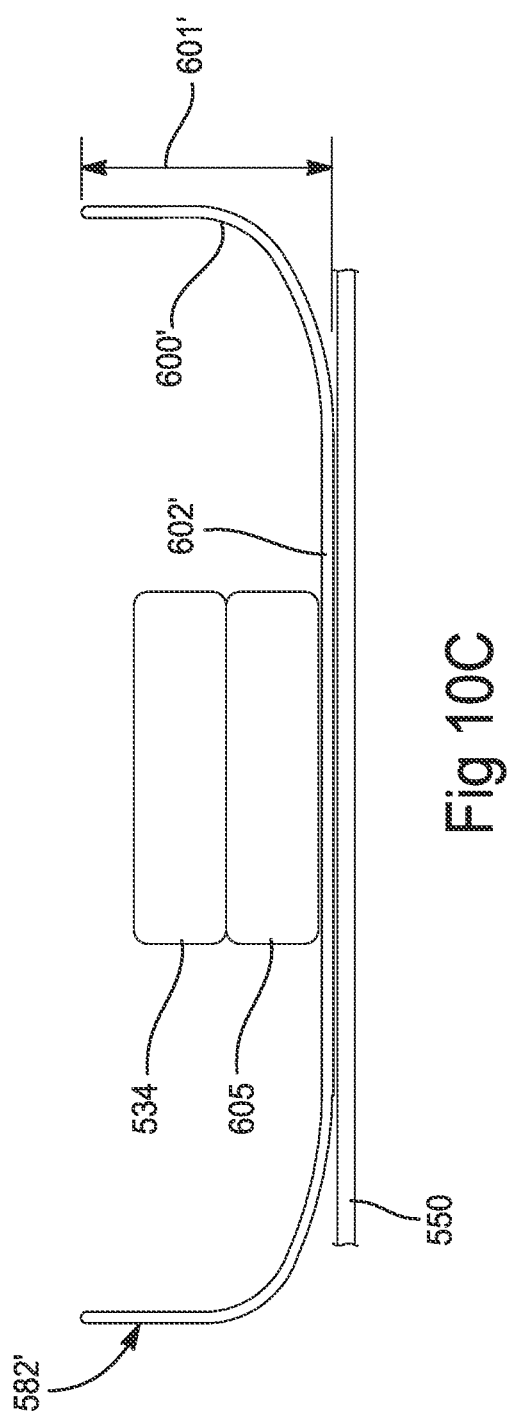
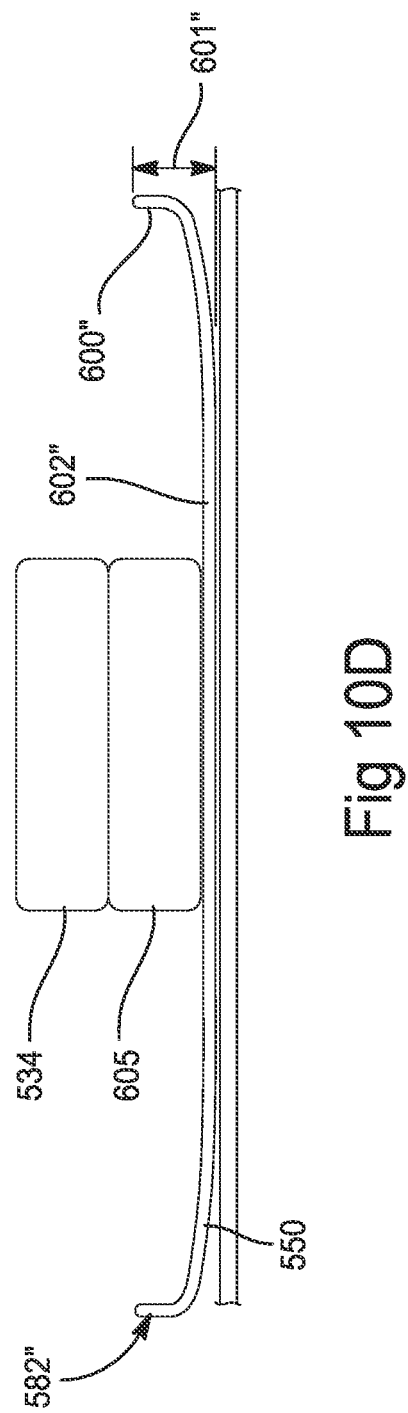

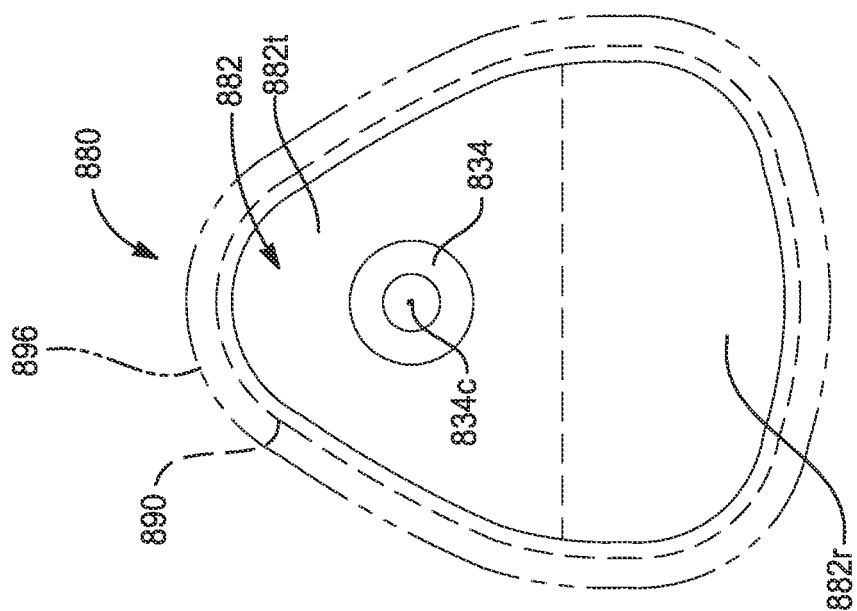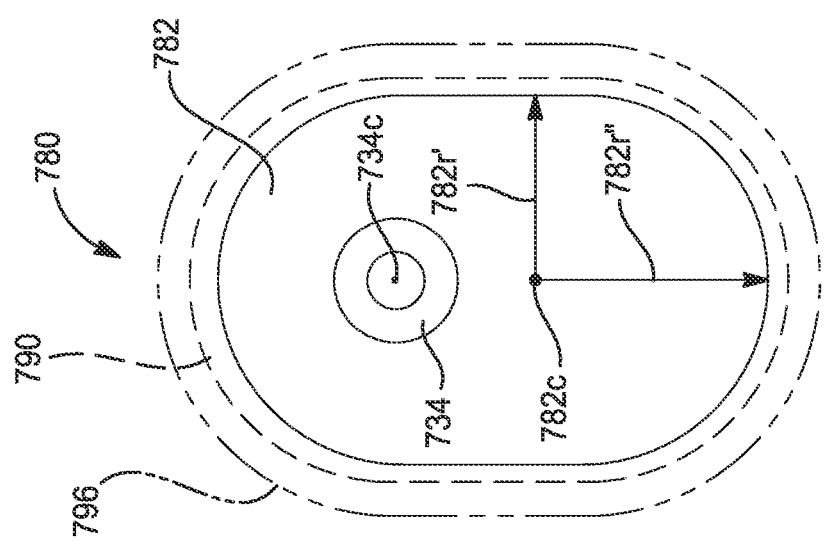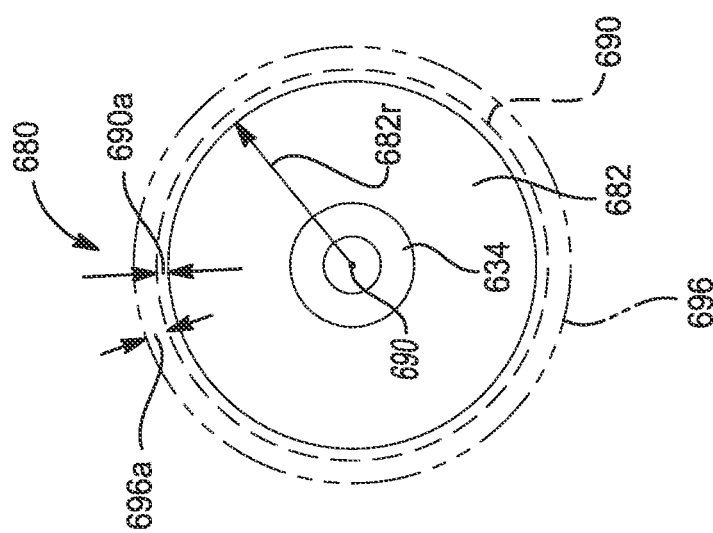

NAVIGATION SYSTEM AND METHOD

CROSS-REFERENCE TO RELATED APPLICATIONS

This application is a divisional of U.S. application Ser. No. 17/064,813 filed Oct. 7, 2020 which is a continuation of U.S. application Ser. No. 15/957,539, filed on Apr. 19, 2018, now U.S. Pat. No. 11,564,747 issued Jan. 31, 2023, which claims the benefit of U.S. Provisional Application No. 62/487,801, filed on Apr. 20, 2017. The entire disclosure of each of the above applications are incorporated herein by reference.

FIELD

The subject disclosure relates generally to a system for generating a field, and particularly to a system and arrangement to generate a selected electro-magnetic field.

BACKGROUND

This section provides background information related to the present disclosure which is not necessarily prior art.

In a navigation system for various procedures, such as surgical procedures, assembling procedures, and the like, an instrument or object may be tracked by measuring an effect of a magnetic field on a sensor coil. The sensor coil may include a conductive material that is placed within a magnetic field where a current is induced on the coil. The measured induced current may be used to identify or determine a location of the instrument or object. Determining the location of a coil, however, may be desired to be enhanced in various aspects.

The electro-magnetic field or fields may be generated with a plurality of purposefully positioned and oriented transmit coils. Various transmitter or field generation systems include the AxiEM™ electro-magnetic navigation system sold by Medtronic Navigation, Inc., having a place of business in Louisville, Colo. The AxiEM™ electro-magnetic navigation system may include a plurality of transmit coils that are used to generate one or more electro-magnetic fields that are sensed by a tracking device, which may be sensor coil, to allow a navigation system, such as a StealthStation® surgical navigation system to be used to track and/or illustrate a tracked location of an instrument.

The transmit coils positioned and oriented about one another generally fill a volume smaller than a navigation volume generated by the transmitting coils. The volume including the transmitting coils, however, is generally positioned near the patient so that the navigation field or volume encompasses a region of the patient in which navigation would occur. Accordingly, the transmitter coil array may be near an individual, such as a surgeon, performing a procedure.

SUMMARY

This section provides a general summary of the disclosure, and is not a comprehensive disclosure of its full scope or all of its features.

Disclosed is a localizer, which may include a transmitting assembly, particularly a transmitting coil array (TCA), and a field shaping assembly that is configured and is operable to transmit one or more diverse magnetic field or fields. Particularly, the localizer is configured to generate field vectors that are highly diverse relative to one another with a relatively orthogonal or near orthogonal distribution of measurable vectors relative to an origin or within a volume. The diversity of one or more fields is generated even though a plurality of coils of the TCA are positioned on a substantially flat plane. The accuracy, precision, and reliability of a determined location of a sensor, such as a coil, may be improved with additional measurements, particularly additional measurements of effects of one or more of the diverse magnetic fields on a sensor coil.

The localizer may be formed of a plurality of cooperative features including the transmitting/transmitter coil array (TCA) including one or more transmitting coils and a field shaping assembly. The field shaping assembly is provided to include a plurality of portions or members that separately interact with the magnetic field produced by one or more of the coils. For example, a plurality of coils may be formed as one or more trios or triplets of coils that are all powered to generate a field. A field shaping segment may be provided to interact substantially individually with the field. The TCA, therefore, may generate or form a generated navigation field in a navigable volume that may substantially mimic a field created by co-center positioned and orthogonally oriented coils. The TCA, therefore, may include a substantially low profile, or flat configuration, and be positioned near or adjacent a location without being intrusive in an operating theater. For example, the TCA may be positioned under a patient or between a patient and a support structure.

The field shaping assembly may be included with or fixed relative to the TCA. The TCA and field shaping assembly may also be referred to as a localizer. The field shaping assembly may be used to affect a generated field to create the second field configuration for ensuring a diversity of the field. The field shaping assembly may also acts to mitigate or eliminate effects of external conductive surfaces and materials, such as conductive metal, which may be present in a support structure or in other structures away from the localizer. For example, the TCA may be positioned on a surgical operating bed that may include metal or other conductive materials where the field shaping assembly ensures that the conductive materials do not affect or substantially affect the field produced by the localizer. In various embodiments, substantially affecting the field produced by the localizer may include where a conductive material may be present near the localizer, but no compensation (e.g. processing or algorithmic compensation) need occur to allow for an appropriate and accurate tracking of a selected tracking device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is an exploded view of a localizer;

FIG. 3 is a top plan view of a localizer structural component;

FIG. 4 is a cross-sectional view along line 4-4 of FIG. 3;

FIG. 4A is a detailed cross-sectional view of FIG. 4;

FIG. 5A is a plan view of a field shaping assembly;

FIG. 5B is a cross-sectional view of a conductive member;

FIG. 5C is a cross-sectional view of the magnetically permeable member;

FIG. 10C is a cross-section of a field shaping assembly and a coil, according to various embodiments;

FIG. 10D is a cross-section of a field shaping assembly and a coil, according to various embodiments;

Figure 12A:
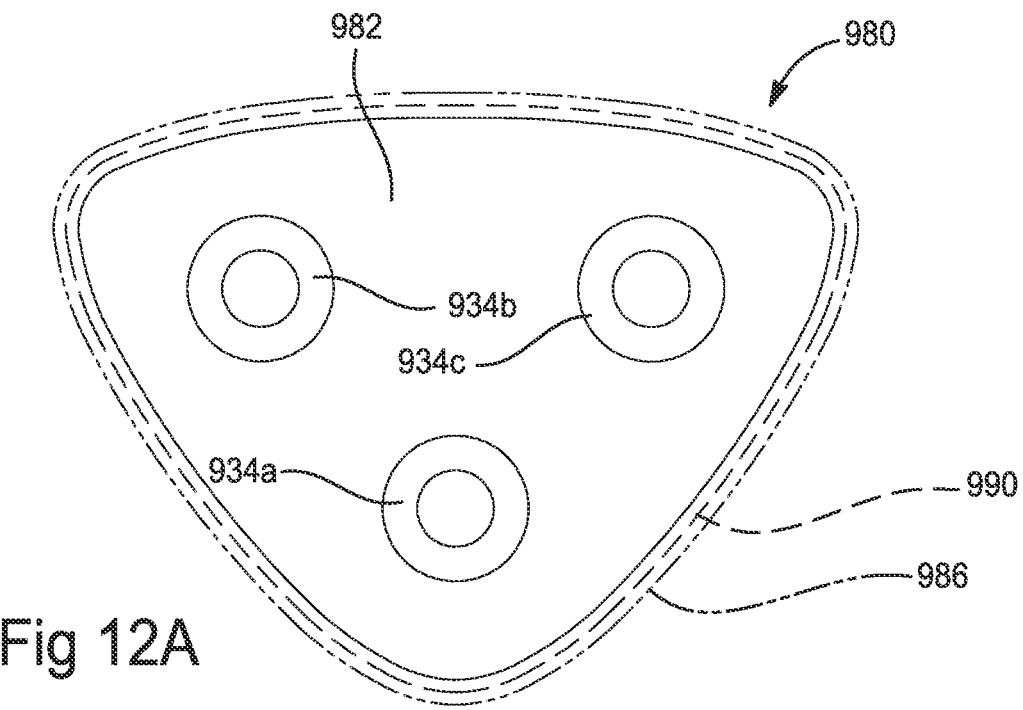
Figure 12B:
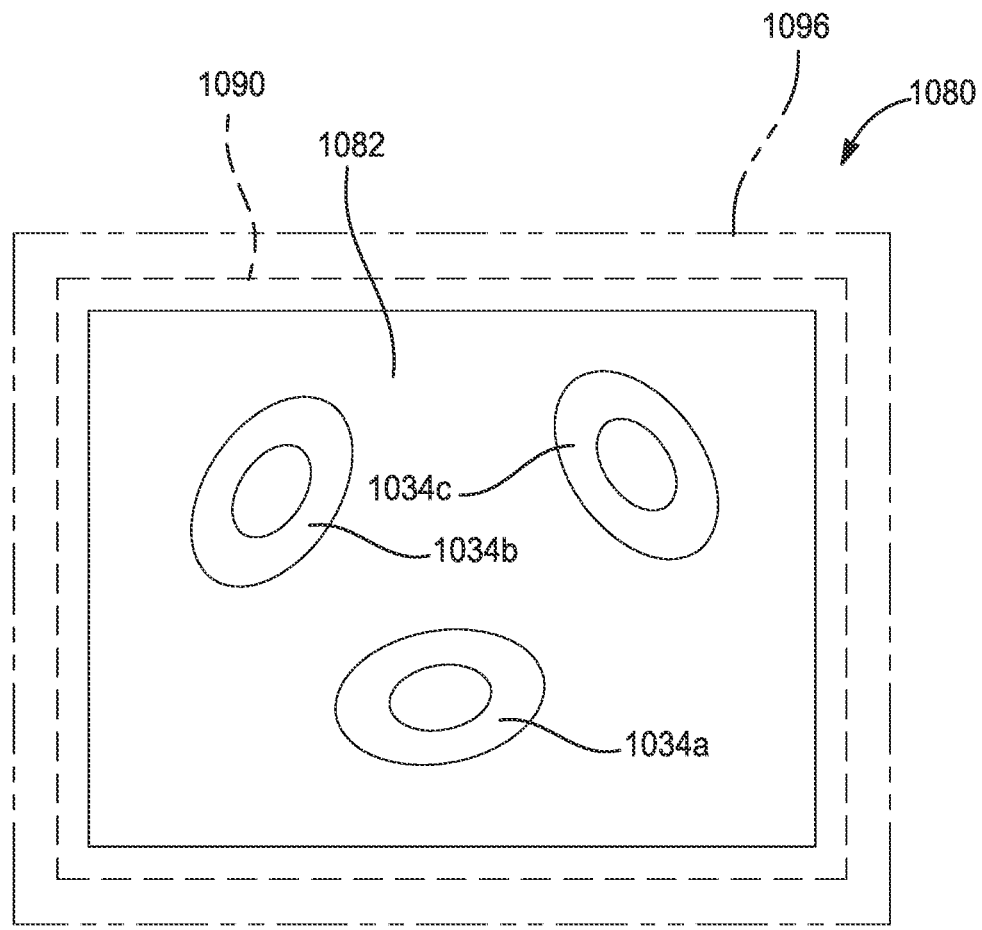
Figure 13:
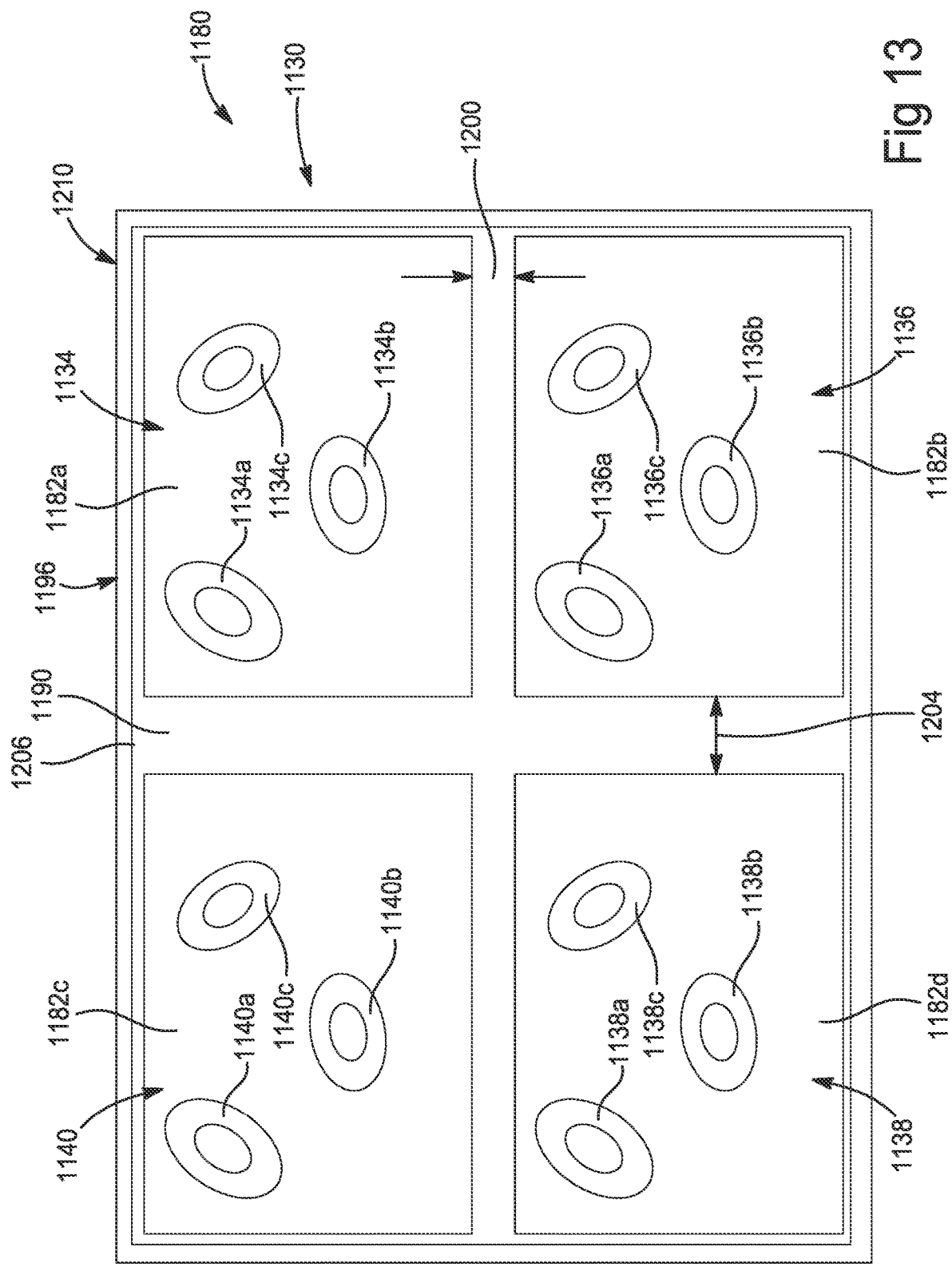

FIG. 11A, FIG. 11B, and FIG. 11C illustrate a field shaping assembly with a single coil, according to various embodiments;

FIG. 12A and FIG. 12B illustrate field shaping assemblies with a plurality of coils positioned relative thereto, according to various embodiments; and FIG. 13 illustrates a field shaping assembly including a plurality of coils positioned relative thereto, according to various embodiments.

Corresponding reference numerals indicate corresponding parts throughout the several views of the drawings.

DETAILED DESCRIPTION

Example embodiments will now be described more fully with reference to the accompanying drawings.

A navigation system 10 (FIG. 9), which may include a localizer assembly or system 20 as illustrated in FIG. 1, may be used for various purposes or procedures. A navigation system may be used to determine or track a location of an instrument in a volume. Tracking a location of an instrument may assist a user in determining a location of the instrument, even if the instrument is not directly viewable by the user. A location may include at least one three-dimensional position (e.g. X, Y, or Z coordinates) and at least one orientation (e.g. yaw, pitch, and roll). In various embodiments, therefore, location may include six-degrees of freedom. Various procedures may block the view of the user, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject and the procedure may be performed on a human patient.

Figure 9:
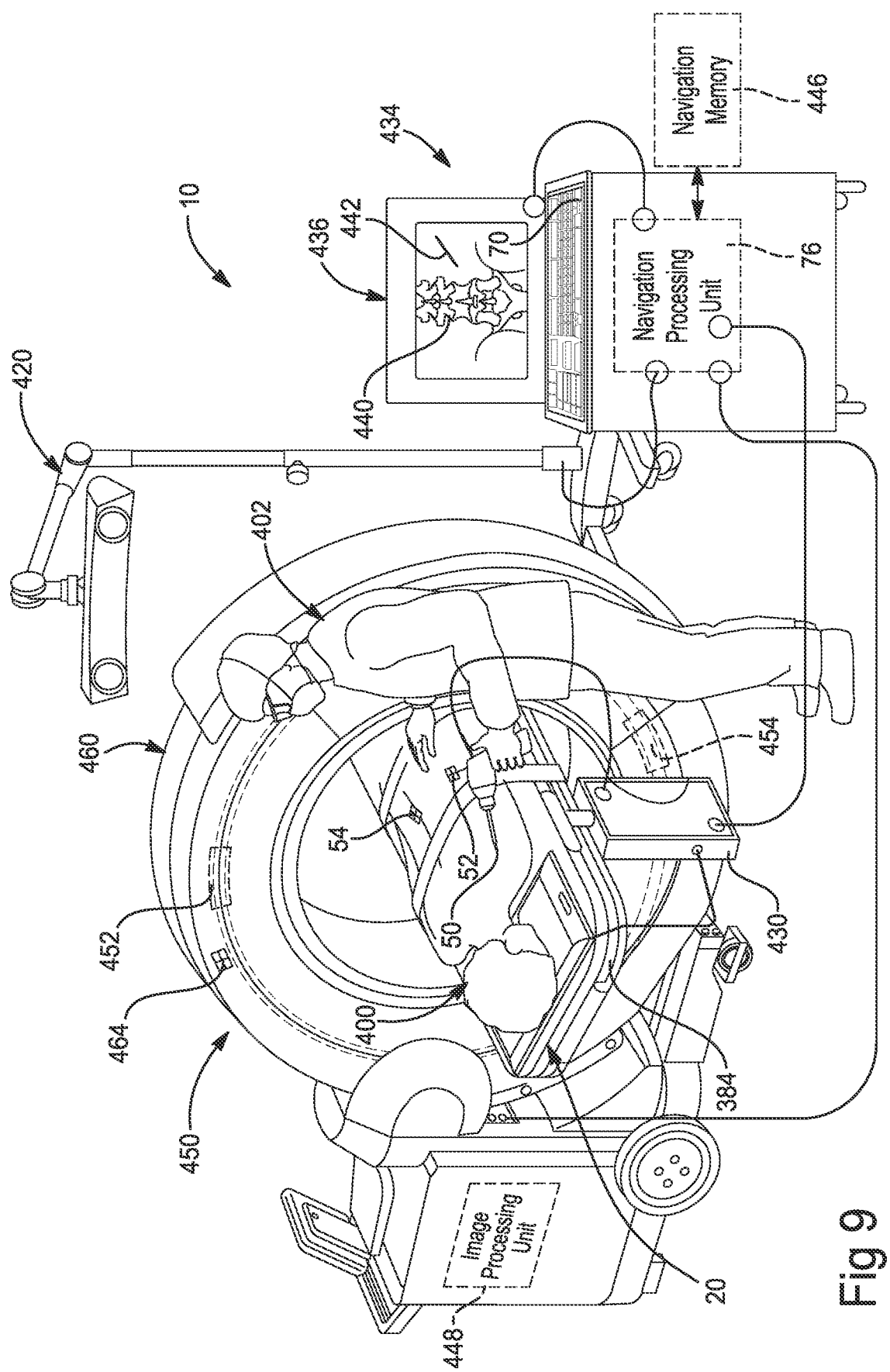
FIG. 9 is an environmental view of a navigation system.

Nevertheless, in various embodiments, a surgical navigation system 10 (FIG. 9), as discussed further herein, may incorporate a various portion such as those disclosed in U.S. Pat. Nos. RE44,305; 7,697,972; 8,644,907; and 8,842,893; and U.S. Pat. App. Pub. Nos. 2004/0199072, all incorporated herein by reference. Various components of a surgical navigation system may include an imaging system that is operable to image a patient, such as an O-arm® imaging system, magnetic resonance imaging (MRI) system, computed tomography system, etc. Images may either be acquired during a surgical procedure or acquired prior to a surgical procedure for displaying on a display device. An instrument may be tracked in a trackable volume or a navigational volume that is produced by a transmitter or transmitting coil array that is incorporated into a localizer 20, as illustrated in FIG. 9.

Figure 6:
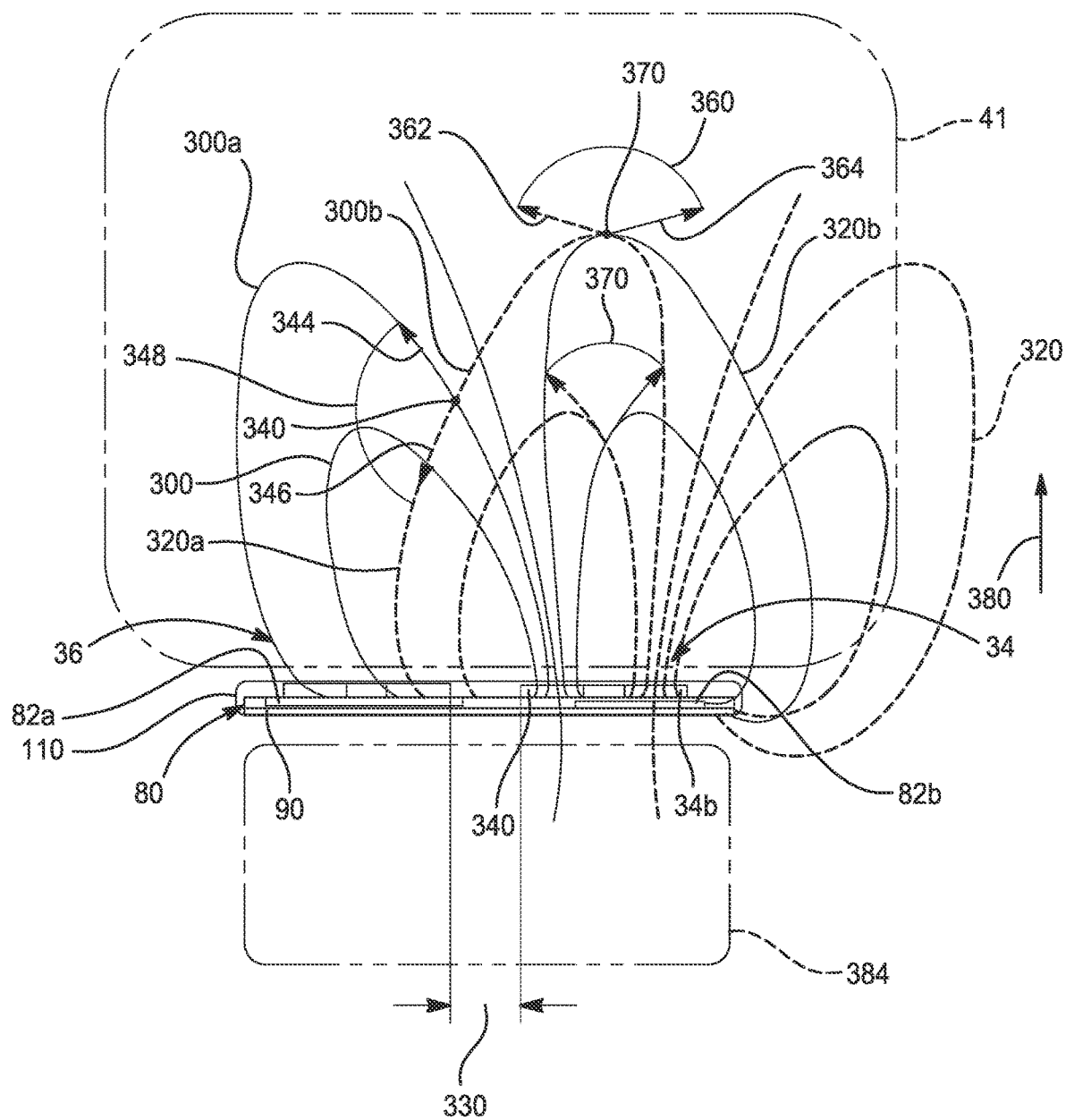
FIG. 6 is a schematic view of a localizer including representative field lines.

With reference to FIG. 1, the localizer 20 may be an electro-magnetic (EM) localizer that is operable to generate electro-magnetic fields with a transmitting coil array 30. The coil array 30 may include one or more coil groupings or arrays such as a first grouping 34, a second grouping 36, and a third grouping 38, and a fourth grouping 40. Each of the groupings may include three coils, also referred to as trios or triplets. For example, the first grouping 34 may include a first coil 34a, a second coil 34b, and a third coil 34c. Similarly, the second grouping 36 may include a first coil 36a, a second coil 36b, and a third coil 36c. The third grouping 38 may include first coil 38a, a second coil 38b, and a third coil 38c. A fourth grouping 40 may include a first coil 40a, a second coil 40b, and a third coil 40c. The coils may be powered to generate or form an electro-magnetic field by driving current through the coils of the coil groupings 34, 36, 38 and 40. As the current is driven through the coils, the electro-magnetic fields generated will extend away from the coils 34, 36, 38, and 40 and form a navigation domain or volume 41 (e.g. as illustrated in FIG. 6).

The navigation domain or volume generally defines a navigation space or patient space. As is generally understood in the art, an object or instrument 50, such as a dill, lead, etc., may be tracked in the navigation domain relative to a patient or subject with an instrument tracking device 52. For example, the instrument 50 may be freely moveable, such as by a user, relative to a dynamic preference frame (DRF) or reference frame tracker 54 that is fixed relative to the subject. Both the tracking devices 52, 54 may include sensing coils (e.g. formed as coiled conductive material sensors) that sense and are used to measure a magnetic field strength, etc. Due to the tracking device 52, connected or associated with the instrument 50, relative to the DRF 54 the navigation system 10 may be used to determine location of the instrument 50 relative to the DRF 54. The navigation volume or patient space may be registered to an image space of the patient and an icon representing the instrument 50 may be superimposed on the image. Registration of the patient space to the image space and determining a location of a tracking device, such as the tracking device 52, relative to a DRF, such as the DRF 54 may be performed as is generally known in the art, including as disclosed in U.S. Pat. Nos. RE44,305; 7,697,972; 8,644,907; and 8,842,893; and U.S. Pat. App. Pub. Nos. 2004/0199072, all incorporated herein by reference.

With continuing reference to FIG. 1, the localizer 20 may further include a printer circuit board (PCB) 60 that includes traces thereon from a cable connector 62 to which a communication or power cable 64 may be connected. The traces on the PCB 60 may connect the cable 64 with individual cable connectors 66, 68, 70, and 72. The connectors may include leads or wires that may be connected to each of the coils in coil groups 34, 36, 38, and 40. Accordingly, the coils in coil groups 34, 36, 38, and 40 may be powered or driven by power provided through the traces on the PCB 60 to each of the coils in coil groups 34, 36, 38, and 40, from a navigation processor system 76. The navigation processor system may include those disclosed in U.S. Pat. Nos.

RE44,305; 7,697,972; 8,644,907; and 8,842,893; and U.S. Pat. App. Pub. Nos. 2004/0199072, all incorporated herein by reference, or may also include the commercially available StealthStation® or Fusion™ surgical navigation systems sold by Medtronic Navigation, Inc. having a place of business in Louisville, Colo.

The localizer 20 further includes a field shaping assembly 80. The field shaping assembly 80 may generally include a first magnetically permeable portion that is also substantially nonconductive 82, a spacer 86 which may be substantially inert, and a substantially conductive portion 90. The magnetically permeable magnetic portion 82 may include various properties, such as being generally highly magnetically permeable, substantially nonconductive, high magnetic saturation, low magnetic coercivity, as discussed further herein. The spacer member 86 is substantially inert relative to an electric current and a magnetic field and may include a polymer or plastic material such as a polycarbonate having a thickness of about 0.001 millimeters (mm) to about 10 mm, including about 1.0 mm. The thickness of the spacer 86 generally defines a distance between the magnetically permeable member 82 and the conductive member 90. The magnetically permeable magnetic portion 82 may be provided as four individual portions or members 82a, 82b, 82c, and 82d, as discussed further herein. The individual members may be positioned near each of the coil groups 34, 36, 38, and 40 and near corners of the conductive member 90. The conductive member or portion 90 generally includes a highly conductive material such as a high purity copper or other appropriate highly conductive material. The conductive member 90 may allow generation of eddy currents formed by induced currents due to magnetic fields permeating into the conductive material 90.

Figure 2A:
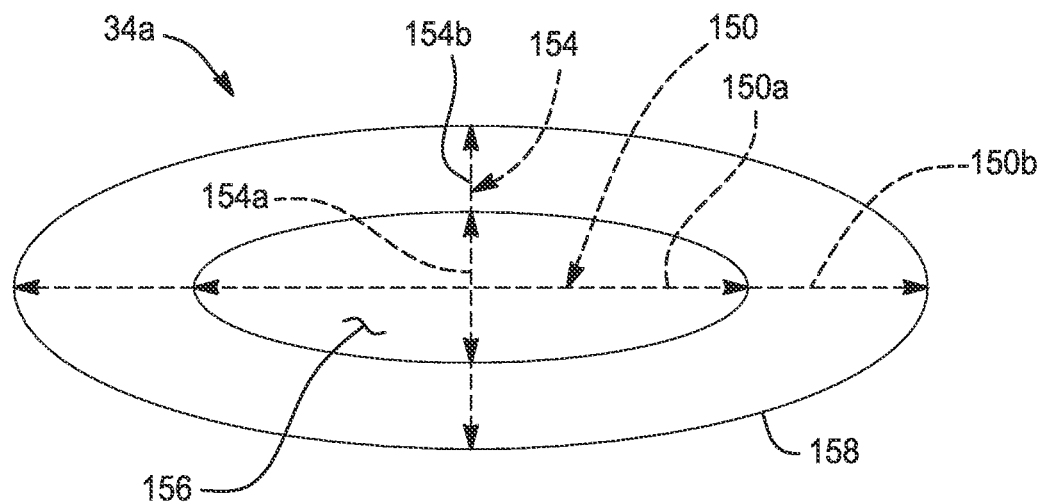
FIG. 2A is a top view of a coil of a transmitting coil array.

The localizer 20 may further include two shells or cover portions including a first cover portion 100 and a second cover portion 104. The two cover portions enclose all of the coil array 30, the field shaping assembly 80, and a structural or holding component 110. Further, various feet or non-skid elements 116 may be adhered or connected to the case portion 104 for selected operational uses. Moreover, the case, such as the first case portion 100 may include select ergonomic and carrying portions including a hand hole or region 120 and shaped ergonomic portions. Shaped portions may include a neck support region 124 having lower or indent portions 126 and 128 to assist in holding or positioning a head or neck region of a patient or subject for selected procedures. It is understood, however, that the shape and configuration of the cover 100 may be formed in any appropriate shape. Further, the localizer 20 may have selected dimensions of length 20a, width 20b, and height 20c. The length 20a may be about 400 mm to about 600 mm, including about 450 mm to about 550 mm, including about 510 mm. The width 20b may be about 400 mm to about 500 mm, including about 3000 mm to about 400 mm, including about 355 mm. The height 20c may be about 10 mm to about 55 mm, including about 20 mm to about 50 mm, including about 35 mm. With continued reference to FIG. 1 and additional reference to FIG. 2A and FIG. 2B, the coil array 30 includes the plurality of individual coils, as discussed above. The plurality of coils may be formed into the coil groups 34-40. Each of the coils include various features, as described herein. Further, each coil may include substantially identical or similar features, which will not be repeated for clarity. Thus, an exemplary discussion of coil 34a will be made and it is understood that the other individual coils will have the same or similar features unless otherwise stated.

Figure 2B:
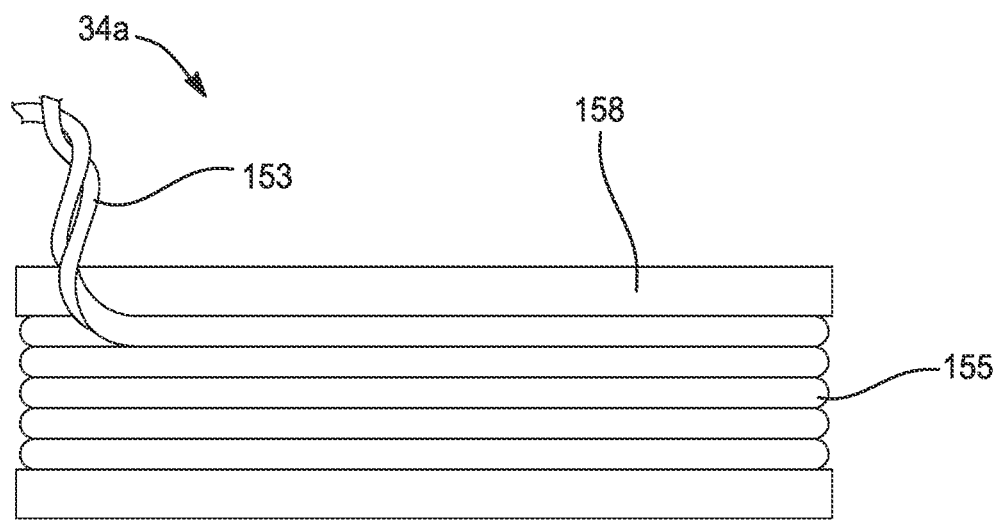
FIG. 2B is a side plan view of the coil FIG. 2A.

The coil 34a may be formed substantially as an ellipsis having a major axis 150 and a minor axis 154. The coil 34a may be formed on a mold or form and then removed as including substantially only the coiled with or conductive portions. The coil, however, may include the dimensions as discussed herein. The coil 34a may, alternatively or in combination, be formed or wound on a bobbin or wire holder. As illustrated in FIG. 2B, the wire may be wound on a bobbin or holder and the combination may be inserted in the structural component 110.

The major axis 150 may include an internal major axis portion 150a having a dimension, such as a length, of about 20 millimeters (mm) to about 50 mm, including about 31 mm to about 35 mm, and further including a dimension of about 33 mm. The major axis 150 may further an external major axis 150b, which includes the internal dimension 150a, that may include a dimension of about 40 mm to about 70 mm, further about 45 mm to about 55 mm, and further including about 50 mm. Thus, along the external major axis 150b the coil 34a may be about 55 mm long.

The minor axis 154 may also include an internal dimension or length of 154a and an external dimension or length 154b, wherein the external dimension 154b includes the internal dimension 154a. The internal dimension 154a may be about 5 mm to about 20 mm, including about 9 mm to about 11 mm, and further including about 10.5 mm. The external dimension of 154b may be about 20 mm to about 40 mm, further including about 22 mm to about 32 mm, and further including about 27 mm. In various embodiments the coil 34a may include an external major axis dimension 150b of about 50 mm and an internal dimension of 150a of about 33.68 mm. Further, the coil 34a may include a minor axis interior dimension 154a of about 10.68 mm and an external dimension 154b of about 27.5 mm.

It is understood that each of the coils of the coil groups 34, 36, 38, and 40 may be substantially identical. Accordingly, each of the coils of the coil groups 34-40 may include dimensions substantially identical to those discussed above.

Further, the coils, such as coil 34a, may be formed by winding selected connective material, such as 21 gage copper magnet wire wound around an outer dimension of the internal major and minor axes. The wire may generally conform to NEMA MW-136C standards. Further, generally the wire may have a single layer of bonded polyurethane nylon insulation. The coil 34a may be formed by winding a pair of leads of the wire. The wire may come to the coil 34a as a twisted pair lead 153, but is not twisted when wrapped around the major and minor internal dimension of the coil as wraps or coil portions 155. The number of windings may include about 5 to about 10 wraps per layer and about 8-15 layers. In various embodiments the coils may include 7 wraps per layer and 12 layers. As discussed above, the external dimensions of the external major and minor axes 150b, 154b may be equal to the external As discussed herein, the combination of the TCA 30 with the selected field shaping components 80 may be used to form a selected field geometry and diversity, as also discussed further herein. The field volume may include a navigable or navigation volume, the navigation volume may be about 400 mm$^3$ to about 600 mm$^3$, including about 500 m$^3$. The navigation field or volume may begin about 50 mm above the TCA 30. It is understood by one skilled in the art that the coils, such as the coil 34a, may be altered depending upon the specifications (e.g. size, type, materials, etc.) of the remaining field shaping components. However, it is understood that the coil 34a may be substantially identical to each of the other coils in the coil array 30 when positioned in the localizer 20.

Each of the coils of the coil groups may be positioned in or on the structural component 110. The structural component 110 may be made of selected materials that generally are inert and do not interact with a magnetic field. Further, the structural component may be made of a non-conductive material. The structural component generally also includes a selected rigidity to provide structural support to the localizer 20.

Figure 3A:
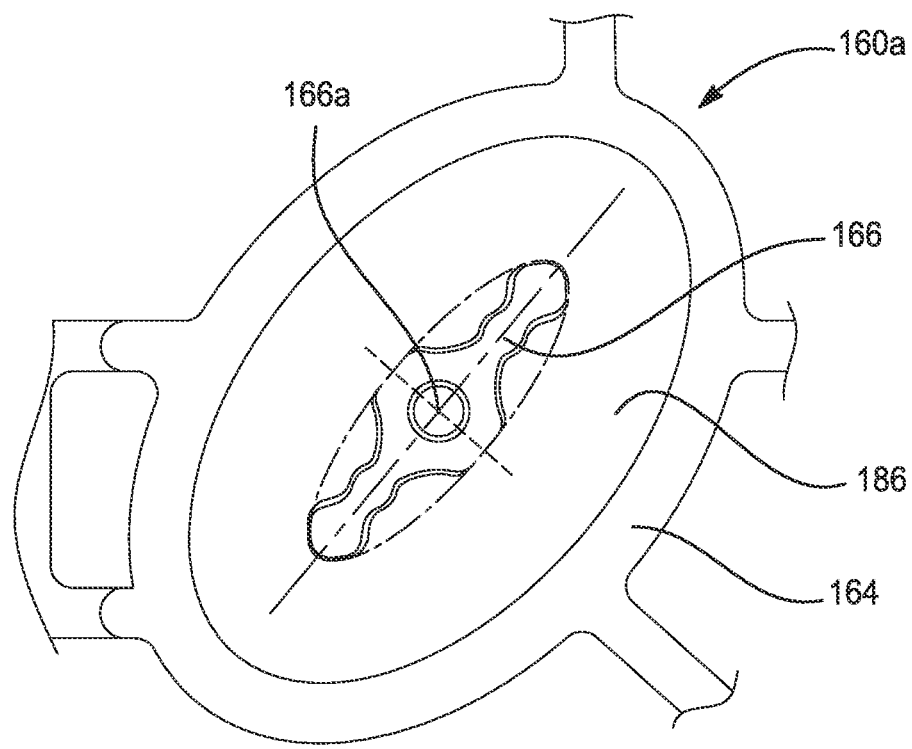
FIG. 3A is a detailed view of a coil holding portion of the structural component.
Figure 3B:
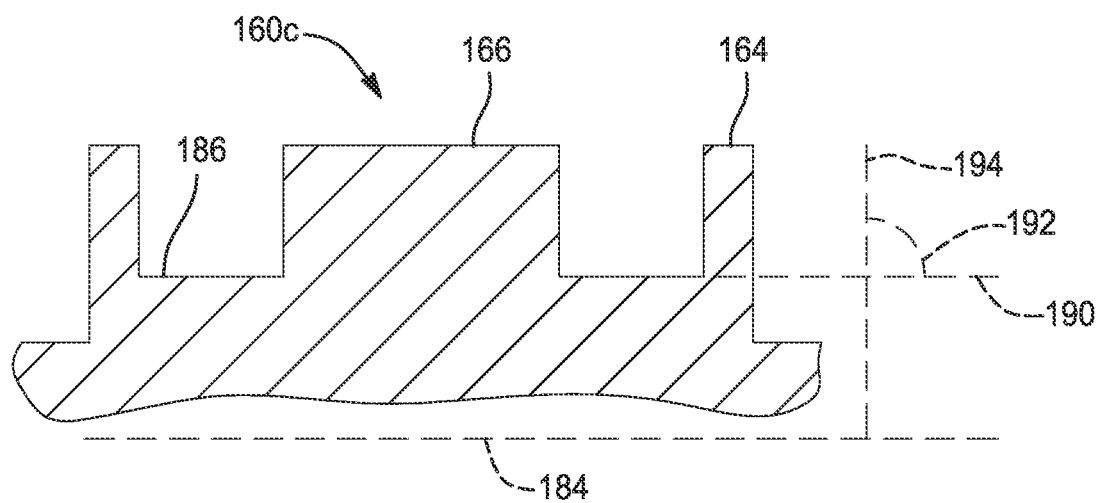
FIG. 3B is a cross-sectional detailed view of a coil holding region of the structural component.

Accordingly, with continuing reference to FIG. 1, and additional reference to FIGS. 3-3B, the structural component 110 will be discussed in greater detail. The structural component 110 may include a plurality of coil holding regions or portions 160, such as twelve coil holding regions 160a, 160b, 160c, 160d, 160e, 160f, 160g, 160h, 160i, 160j, 160k, and 160l. Again, each of the coil holding regions 160a-160l may be configured to form or provide the coil groups 34-40, as discussed above. Accordingly, each of the groupings may include three coils, as illustrated in FIG. 3. For the following discussion, therefore, it is understood that the separate coil groupings may include similar features and components as those discussed below and illustrated in FIG. 3, but are not repeated for clarity of the current discussion. The structural component may have a dimension to fit within the overall dimensions of the localizer 20, including a length 110a of about 450 mm to about 550 mm, including about 450 mm and a width of about 350 mm to about 450 mm, including the width of about 350 mm. The dimensions of the portions containing the coil holding regions or portions 160 may be less than the overall dimensions of the structural component 110 and may be about 330 mm to about 370 mm by about 430 mm to about 470 mm, including about 350 mm by about 450 mm.

With reference to coil holding regions 160a, 160b, 160c, each of these may respectively hold the coils 34a, 34b and 34c. Each coil holding region, such as the coil holding region 160a, illustrated in FIGS. 3A and 3B, may include a raised outer wall 164 that may substantially hold the respective coil 34a in place. Further, a central peg or projection 166 may pass through the central portion 156 of the coil, such as the coil 34a. The peg 166 extends from a floor or bottom surface 186 of the coil holding region 160a. As discussed above, the major internal axis 150a and minor internal axis 154a may define the opening 156 of the coil 34a or a bobbin holding the coiled portions. The projection 166 may pass into or through the opening 156 and the external wall 164 may be near an external surface 158 of the coil 34a or a bobbin holding the coiled portions. Again, it is understood that each coil holding region of the multiple coil holding regions 160 may include similar features.

The coil grouping, such as the first coil group 34, may be positioned around a central point or region 170. The center point or region 170 may be a center point around which each of the coils 34a, 34b, 34c are positioned. Generally, each of the coils 34a, 34b, 34c are radially spaced from the center 170. The coils 34a, 34b, 34c, however, may not all be equally spaced from the center 170 and/or each other. The coils may each be specifically spaced from an edge of the magnetically permeable member over which the respective coil group is placed. In various embodiments, the respective holding regions 160a, 160b, and 160c may be positioned at a selected "clocking angle" relative to one another, such as about 120° from one another around the center 170. It is understood, however, that the respective holding regions 160a, 160b, and 160c need not be 120°, or that all need not be 120° apart.

In various embodiments, for example, the coil holding region 160b may be on an axis or line 172 extending through the center of the coil holding region 160b and the center 170. Similarly, a second axis or line 174 may extend through the center point 170 and a center of the coil holding region 160c. An angle 176 between the two lines 172 and 174 and the angle may be about 120°. It is understood, however, as noted above, that the positioning of the coil holding regions relative to one another may be selected to achieve a selected type of field, such as the appropriate diversity in a field, and, therefore, may be altered from the current illustration. Nevertheless, the coil regions of each of the coil groups 34, 36, 38, and 40 may be formed to hold the respective coils at about 120° from one another around the center point 170. Further, as discussed above and herein, diversity may include diversity relative to time based on a transmitted field from the coil groups and an induced current field from the conductive member 90. Diversity of the field(s) assists in ensuring accurate and/or precise tracking of a selected tracking device.

In various embodiments, the respective coils 34a, 34b, and 34c, in the holding regions 160a, 160b, and 160c may be spaced a selected distance from an edge of the respective magnetically permeable member 82 over which they are placed. The distance may be of an outside edge of the coil to a nearest edge of the magnetically permeable member. The distance may be about 1 mm to about 50 mm, including about 2 mm to about 40 mm, and further 10 mm to about 40 mm, and further including about 20 mm to about 25 mm. Another distance may be of an outside edge of the coil to a farthest edge of the magnetically permeable member. This distance may be about 30 mm to about 120 mm, including about 50 mm to about 100 mm.

In various embodiments, in additional to and/or in combination with those discussed above, the respective coils 34a, 34b, and 34c, in the holding regions 160a, 160b, and 160c may be spaced a selected distance from a corner and/or edges of the respective magnetically permeable member 82 over which they are placed. The respective coils 34a, 34b, and 34c and/or the holding regions 160a, 160b, and 160c may be positioned around the common center 170. A center of the coils 34 and/or the center 166a of the coil holding regions 160 may be placed about 10 mm to 50 mm including about 30 mm to about 40 mm from the common center 170. Further, the center of the coils 34 and/or the center 166a of the coil holding regions 160 may be spaced apart at a distance of about 20 mm to about 100 mm including about 50 mm to about 80 mm from each other. Also, the center of the coils 34 and/or the center 166a of the coil holding regions 160 may be a distance from a nearest boundary edge of the magnetically permeable member 82, the distance may be about 20 mm to about 100 mm including about 40 mm to about 70 mm from the nearest boundary. The center of the coils 34 and/or the center 166a of the coil holding regions 160 may sit about 80 degrees to about 160 degrees including about 120 degrees around the common center 170. One of the coil centers may sit about 0 degrees to about 20 degrees from a diagonal of the magnetically permeable member 82. The long or major axis 150 axes of the coil 34a may vary from about 0 to about 90 degrees to the nearest boundary line or tangent line of the magnetically permeable member 82. It is understood that each of the coils of the various coil groups 34, 36, 38, and 40 may be configured as discussed above. Further, each may be varied to achieve a selected field geometry.

With continuing reference to FIG. 3 and with further reference to FIG. 3B, the coil holding regions may also include a geometry relative to a substantially flat plane 184. As discussed further herein, the flat plane 184 may be any appropriate plane, such as one defined by a surface of the field shaping portion 80, especially defined by a surface of the magnetically permeable portion 82.

The coil holding region 160c may include a bottom surface 186, as also illustrated in FIG. 3, upon which the coil, such as the coil 34c, may rest when positioned in the structural component 110. The bottom surface 186 of the coil holding portion 160c contacts or holds the coil 34a in a position and orientation, the bottom surface 186 may define a plane 190 that orients or positions the coil 34a relative to the plane 184. The plane 190 may be parallel or at an angle that will intersect the plane 184, such as about zero degrees (°) to about 70°, including about 90°, further including about 0° to about 60°. In various embodiments, the plane 190 defined by the bottom surface 186 may extend at an angle 192 relative to a line 194 that is normal to the bottom plane 184. The angle 192 may be about zero degrees (°) to 180°, including about 90° and further including about 30° to about 150°, including about 90°. In various embodiments, each of the coil holding regions 160a-160l may include the angle 192 that is the same, in various embodiments, however, at least one of the holding regions 160a-160l may include the angle 192 that is different from the others. Further, it is understood that the bottom surface 186 of the respective coil holding regions 160a-160l may tilt along the major axis of the respective coil, the minor axis of the respective coil, or a combination thereof. In various embodiments, therefore, the coil 34a may be positioned relative to the plane 184 in any appropriate angle. Thus, the coil 34a may not have a top or bottom surface that is substantially parallel with the plane 184. Rather, the coil 34a, may be tilted relative to the plane 184. As discussed further herein, the positioning of the coil 34a relative to the plane 184 may be a position of the coil 34a relative to a plane defined by the magnetically permeable field shaping portion 82 to assist in forming or generating a selective field diversity. Again, as discussed above, each coil holding portion 160 may include similar or identical features and dimensions, as discussed above.

With additional reference to FIG. 4 and FIG. 4A, and continuing reference to FIG. 3, the structural component 110 includes a field shaping assembly contact or holding side 114 that is opposite the coil holding side 112. The field shaping assembly holding side 114 of the structural component 110 may include various features such as a main or expansive pocket 200 that has a main surface or base surface 202 and a wall 204 that extends from the main surface 200. The wall 204 may assist in holding the conductive member 90 relative to the coil array 30. The conductive member 90 is formed as or configured as a single (e.g. one) piece of material. In various embodiments, the conductive member 90 may be formed as a plurality of members that are electrically connected or electrically isolated over the entire surface of the expansive pocket 200.

The coils of the coil array 30 are held in the coil holding portions 160a-160i while the main surface 202 and the upstanding wall 204 assist in holding the conductive member 90 relative to the coil array 30. The upstanding wall 204 may have a dimension that is substantially equivalent to or has an interference fit with the conductive member 90. Further, various adhesives or holding materials or members (e.g., rivets, screws, or the like) may be used to fix or hold the conductive member 90 relative to the structural component 110.

The structural component 110 may further include a pocket 220, which may be referred to as a small or coil group pocket 220. The small pocket 220 may include a main surface 222 and an upstanding wall 224. The upstanding wall may extend from the main surface 222 to the surface 202 of the conductive pocket 200. The upstanding wall 224 may have a dimension that is substantially equivalent to an exterior dimension of the magnetically permeable component 82. The spacer component 86 may have a dimension that is equal to or slightly larger than the upstanding wall 224. Therefore, the conductive member 90 may press the spacer component 86 onto the magnetically permeable component 82 and the surface 202 of the conductive pocket 200 to assist in holding the spacer material 86 in place. Further, a force may be applied against the magnetically permeable component 82 as the conductive member 90 is pressed against the spacer component 86, which, in turn presses against the magnetically permeable component 82 into the small pocket 220.

It is understood that each of the coil groupings, including the coil grouping 34, 36, 38, and 40 may each include a separate pocket. As illustrated in FIG. 1, and discussed further herein, the magnetically permeable component 82 may be formed as an individual unit or member (or laminated members of the same perimeter dimensions) for each of the coil groups or trios 34, 36, 38, and 40. Accordingly, each magnetically permeable component 82 may be positioned in a separate one of the pocket 220. The structural component 110 by defining or forming the pockets 220, therefore, may provide a physical spacing between each of the magnetically permeable component 82. Generally, the pockets 220 are formed to hold the magnetically permeable members 82 near the coil group 34, but not in contact with another magnetically permeable member 82. The magnetically permeable members 82 may be spaced a distance 330', 330" (FIG. 5A) apart. The distances 330', 330" may be about 1 mm to about 200 mm apart including about 1 mm to about 100 mm apart, including about 10 mm apart.

It is understood that each of the elements, including the TCA 30 the magnetically permeable component 82, spacer 86, and electrically conductive member 90 may be adhered or affixed to the structure component 110 in a selective manner. For example, an adhesive or epoxy, such as Locktite® brand adhesive or epoxy may be used to fix all or portions of the coils and field shaping components 80 to the structural component 110. Accordingly, each coils of the TCA 30 and the field shaping components 80 may be substantially fixed in a three-dimensional space relative to one another when affixed to the structural component 110.

The field shaping assembly members 80, as illustrated in FIG. 1, include various components and members and discussed further herein. As discussed above the TCA 30, including the various individual coil members or portions, may be driven to generate an electro-magnetic field. The electro-magnetic field may extend from the TCA 30 as is generally understood by one skilled in the art. As discussed above, the electro-magnetic field may affect tracking devices, such as the instrument tracking device 52 and/or the DRF tracking device 54. The electro-magnetic field is sensed by the tracking devices 52, 54 and a position of the tracking devices 52, 54 may be determined relative to one another. The shell or case components 100, 104 may be substantially inert and/or not affect the electro-magnetic field. In various embodiments the shell portions 100, 104 may be substantially electrically resistive as well.

With continued reference to FIG. 1 and additional reference to FIGS. 5-5B, the field shaping assembly 80 may include the magnetic or magnetically permeable portion or portions 82, the substantially inert spacer portions 86, and the conductive member 90. As illustrated in FIG. 1, FIG. 5A and FIG. 5B, the conductive member 90 may include a first surface 260 that has a surface area. The surface area of the surface 260 may be substantially continuous and extend or be defined by the length of a first edge 262 and a second edge 264. As is generally understood in geometry, the surface area of the surface 260 may be the two lengths 262, 264 multiplied together.

The magnetically permeable member 82 may be provided as a plurality of magnetically permeable members 82a, 82b, 82c, and 82d. Each of the magnetically permeable members 82 may be substantially similar or identical in size and may include respective first surfaces 270a, 270b, 270c, and 270d. Each of the surfaces 270 may include substantially similar surface areas and be bounded by respective edges 274 and 276. Again, as understood in geometry, the surface area of the respective surfaces 270, would be the dimension of the edge 274 multiplied by the dimension of the edge 276.

The magnetically permeable members 82 may be sized and dimensioned to be positioned relative to each of the coil groups 34, 36, 38, 40. For example, with reference to FIG. 5A, the coils 32a, 32b, and 32c (illustrated in phantom) may be positioned on the structural member 110 on the coil array side 112. The structural member may separate the coil 34a, 34b, 34c physically from the magnetically permeable member 82a, but a magnetic field produced by the coil group 34 may be affected by the magnetically permeable member 82a and the conductive member 90. Again, it is understood that the coils 34a, 34b, 34c may be positioned about 120 degrees apart, such that the axis 172 extending through a center of the coil 34b and the center 170 and the second axis 174 extending through the center 170 and the center of the coil 34a are positioned at the angle 176 from one another. The angle 176 allows each of the coils 34a, 34b, 34c to be positioned around the center 170 separated by about 120°.

It is further understood that the spacers 86 may be positioned between the conductive member 90 and each of the magnetically permeable members 82a, 82b, 82c, and 82d. It is understood that the spacer 86 may be provided as a large single spacer member that has a surface area that covers an area equivalent to an exterior dimension defined by all of the magnetically permeable members 82 and/or the conductive member 90, alternatively or in addition thereto an individual spacer member may be provided for each of the magnetically permeable members 82. The spacer member 86 is substantially inert to both electrical current and magnetic fields. The spacer member 86, therefore, may be formed in a manner for efficient assembly and manufacturing, thus one spacer member may be provided for each of the magnetically permeable members 82, rather than a single large spacer member.

The conductive member 90, with additional reference to FIG. 5B, may be selected of an appropriately electrically conductive material. The electrically conductive material may include a copper sheet of high purity, such as copper sheet C101A-02 that meets material standards ASTN F-68. The conductive sheet 90 may be an appropriate thickness 279 such as about 0.5 mm to about 3 mm, including about 1 mm to about 2 mm, and further including about 1 mm. The conductive member 90 may further have the side 262 having a length of about 400 mm to about 500 mm, further including about 420 mm to about 450 mm, further including about 438.5 mm to 439.5 mm, and further including about 439 mm. The edge or side 264 may have a dimension of about 320 mm to about 350 mm, further including about 335 mm to about 345 mm, further including about 338.6 mm to about 339.2 mm, and further including about 338.9 mm.

The magnetically permeable members 82 may be selected from any appropriate highly magnetically permeable material that is substantially nonconductive and has high magnetic saturation as well as low magnetic coercivity and low frequency dispersion. For example, the magnetically permeable members may be formed of Finemet® nanoparticle crystalline material sold by Hitachi Metals, Ltd. having a place of business in Tokyo, Japan and Novi, Mich. The magnetically permeable member 86 may include the Finemet® material having a manufacturer number MS-FR code FIAH0535. Generally, each magnetically permeable member 86 may be formed of a plurality of layers of the Finemet® nanoparticle crystalline material laminated together and held together with a selected adhesive. It is understood that magnetic permeable materials may include appropriate or selected materials such as Finemet® nanoparticle crystalline material, METGLAS® magnetic permeable materials Magnetic 2605SA1 or 2605HB1 M Alloy sold by MetGlas, Inc. a division of Hitachi Metals America, Ltd.

The magnetically permeable members 82 may have a selected dimension including a length on the sides 274 and 276. For example, the dimension of the side 274 may be about 100 mm to about 200 mm, further including about 156 mm to about 157 millimeters, and further including about 156.50 mm. The side 276 may include a length of about 70 mm to about 190 mm, further including a length of about 132 mm to about 133 mm and further including a dimension of about 132.2 mm. As discussed above, each of the magnetically permeable members 82a, 82b, 82c, and 82d may have substantially identical dimensions.

The magnetically permeable members 82 may be formed as a plurality of layers of the Finemet® magnetically permeable material laminated to one another. The number of laminated layers may be about 8 layers to about 20 layers, including about 11 layers to about 13 layers, and further including about 12 layers. In various embodiments, the number of layers may further include about 15 layers. The layers may be laminated together with a selected piece of material including a substantially electrically and magnetically inert adhesive material. The magnetically permeable members 82, as illustrated in FIG. 5C, may further include a thickness 280 of about 0.1 mm to about 0.2 mm, and further including a thickness 280 of about 0.12 mm.

With reference to FIG. 6, a schematic illustration of magnetic field lines from two coils, for example, coil 34a and 34b are illustrated. The coil 34a is schematically illustrated to produce the solid field lines 300 and the coil 34b includes the dashed field lines 320. The coils 34a and 34b are illustrated in position above or near the field shaping assembly 80 and in the structural component 110. The field shaping assembly 80 includes the components discussed above including the individual magnetically permeable members, such as the magnetically permeable member 82a and the conductive member 90 separated by the spacer member 86. As illustrated in FIG. 6, the coil group 34 is positioned near the magnetically permeable member 82a and the coil group 36 is positioned near the magnetically permeable member 82b. Further, the magnetically permeable members are separated by a space 330. As illustrated in FIG. 6, therefore, the field line 300, 320 may interact with both the magnetically permeable member 82a and the electrically conductive member 90. This allows for a selected diversity of vectors (e.g. different angles between two vectors at a single location in space) defined by the field lines 300, 320, also referred to as field line vectors or field vectors. A diverse field may include a field that has vectors that are about 50 degrees to about 130 degrees relative to one another, including about 54 degrees to about 125 degrees apart, and further including about 54.7 degrees and about 125.3 degrees apart.

In various embodiments, a single point or location in space 340 may be defined by two vectors, a first vector 344 that relates to a field line 300a that is produced by the coil 34a and a second vector 346 that is defined by a field line 320a produced by the coil 34b. The two vectors 344, 346 have an angle 348 between them. This angle may be equal to or greater than 0 degrees to less than or equal to 180 degrees. The two vectors 344, 346 are linearly dependent if the angle is equal to 0 degrees or 180 degrees. The two vectors 344, 346 are linearly independent if the angle is greater than 0 degrees to less than 180 degrees. The two vectors 344, 346 are orthogonal if the angle is equal to 90 degrees. The angle 348 between the vectors 344, 346 may be used in the calculation of the location 340 in a three-dimensional space. The calculation of a position of the point 340 in a three-dimensional space may be similar to that as understood by one skilled in the art and may be based upon a previously determined representation, such as a look-up table, determined and stored based on calibrated field measurements at a plurality of locations in the navigation space, such as defined by the field lines 300, 320.

The angle 348 between the two vectors 344, 346 relative to the lines 300 and 320 may be different than an angle 360 between two vectors 362 defined by a field line 300b and a vector 364 defined by a field line 320b. The different angle 360 between the two vectors 362, 364 may allow for different information regarding a location 370 at the origin of the two vectors 362, 364. Additionally, as illustrated in FIG. 6, the field lines 300, 320 allow for a great diversity of measurable vectors at different locations relative to the coils 34a and 34b in the navigation space 41. With additional reference to FIG. 7, fields may be considered diverse and/or have a selected diversity if, over a set of different locations, a majority of field vector pairs at those different locations are orthogonal or near orthogonal. As an example thereof and/or alternative example, fields may be considered diverse if a majority, including a selected number, of field vector pairs have angles equal to or greater than a selected angle of approximately 54.7° to less than or equal to 180° minus the selected angle or approximately 125.3°. As another example, fields may be considered diverse if a majority of field vector pairs have angles equal to or greater than approximately 50° to less than or equal to about 130°. Without being bound by the theory, but noting the angle range of these examples center around orthogonality at about 90°. Also, diverse fields may provide accurate, precise, and reliable navigation. Fields may be considered not diverse if, over a set of different locations, a majority of field vector pairs at those different locations are linearly dependent or nearly linearly dependent. As an example, fields may be considered not diverse if a majority of field vector pairs have angles equal to or greater than approximately 0° to less than or equal approximately 50° or equal to or greater than approximately 130° to less than or equal approximately 180°.

In various embodiments, the field lines 300, 320 may be substantially diverse and generally extend away from the field shaping assembly 80, such as in the direction of arrow 380. Therefore, the field lines 300, 320 that, along with field lines and fields produced by all of the coils in the TCA 30, may define the navigation space or the navigable volume. Therefore, the navigable space may generally be away from the field shaping assembly 80. The field shaping assembly 80, thus also allows any magnetic field interfering objects positioned generally away from the TCA 30, such as on a side opposite the field shaping assembly 80 from the TCA 30, to not substantially affect the navigable space generated in the direction of arrow 380.

The TCA 30 generally may be operated to transmit in a power range of about 1.0 nano-Watts (nW) to about 1.0 milli-Watts (mW), including about less than 0.1 mW. It is understood, however, that the TCA 30 may be operated to transmit at any appropriate selected power.

Figure 7:
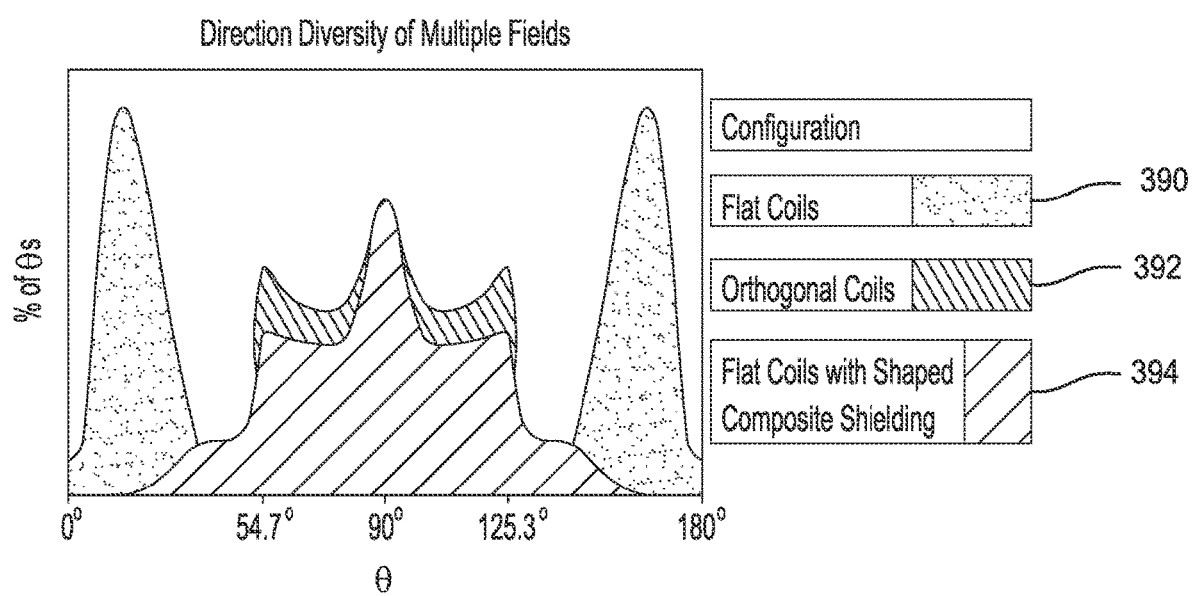
FIG. 7 is an exemplary graphical illustration of diversity of a magnetic field generated with the localizer.

With continued reference to FIG. 6 and further reference to FIG. 7, a graphical representation of possible field diversities is illustrated in FIG. 7. The y-axis represents a percentage of sensed field vectors pair angles over a set of locations and the x-axis represents an angles between two vectors that are determined. The diversity is the difference between two vectors having the same original in space, where the vectors are defined by the field lines of the field generated by the TCA 30.

As illustrated in FIG. 7, if a plurality of transmit coils, such as conductive transmit coils, such as the coils discussed above, are laid substantially flat on a plane without any field shaping the percentage of vectors measured at specific angles is illustrated by the graphical area 390. As illustrated, there is substantially no angular diversity as nearly all vectors have near 0° angular difference or near 180° angular difference. This is understood by one skilled in the art that the field lines are produced substantially in one direction relative to the flat coil array and do not generate a high degree of diversity between field lines. For a coil array positioned in an orthogonal configuration with co-center positioned and orthogonally oriented coil trios, such as a coil array in the AxiEM™ electro-magnetic navigation system, a diversity is illustrated by the graphical area 392 and includes a greater diversity of angle differences between measured field lines from the configured coils. Finally, in various embodiments, the localizer 20, including the TCA 30 and the field shaping assembly 80, has a diversity illustrated by graphical representation 394 as having a large diversity. In other words, the curve of measured angle differences between two vectors at different points is orthogonal or near orthogonal and spread out and not inclusive of only a few angle differences. For example, angles between vectors measured based upon field lines produced by the localizer 20 may have an angle difference between them over a larger broad range, such as about 50 degrees to about 130 degrees between vectors measured at different points. The greater diversity of angles between vectors measured at different points provides additional or greater information for navigation of a tracking device used to measure the fields produced by the coil array 30.

The localizer 20, including the field shaping components 80, is configured to generate the diversity of field lines or angles between vectors defined by field lines as discussed above. In particular, the magnetically permeable members 82 may absorb and redirect a portion of the magnetic field. For example, each layer of the magnetically permeable members 82 may absorb and redirect a certain amount of the field before becoming saturated. Generally the magnetically permeable member 82 is able to absorb and redirect substantially all of the magnetic field that comes in contact with it, but some of the field is from the coil 34a and coil group 34, may leak over and effect the conductive member 90.

However, as noted above, each of the coil groups 34, 36, 38, and 40 includes an individual magnetically permeable portion having a space 333 therebetween. Therefore, at least a portion of the field produced by the coil groups 34, 36, 38, and 40 may interact with the conductive member 90. When a magnetic field interacts with conductive member 90 eddy currents may be generated. In various embodiments, an eddy current may form around the magnetically permeable member 82 on the conductive member 90.

The eddy currents may then also produce electro-magnetic fields that are generally generated and formed in the navigation space. The induced magnetic field produced by the conductive member 90 may be proportional to the time derivative of the field produced by the TCA 30. The induced field produced by the eddy currents in the conductive member 90 may generally be, in terms of complex function of time as is understood by one skilled in the art, out of phase and about 90° out of phase from those produced with the TCA 30. As such, the induced field is diverse (e.g. orthogonal or near orthogonal) to the field produced with the TCA 30. The field produced by the conductive member 90 due to the eddy currents may also be incorporated into navigation space and used by the navigation system 76 to determine location of the tracked member and tracking device, as discussed above.

Figure 8:
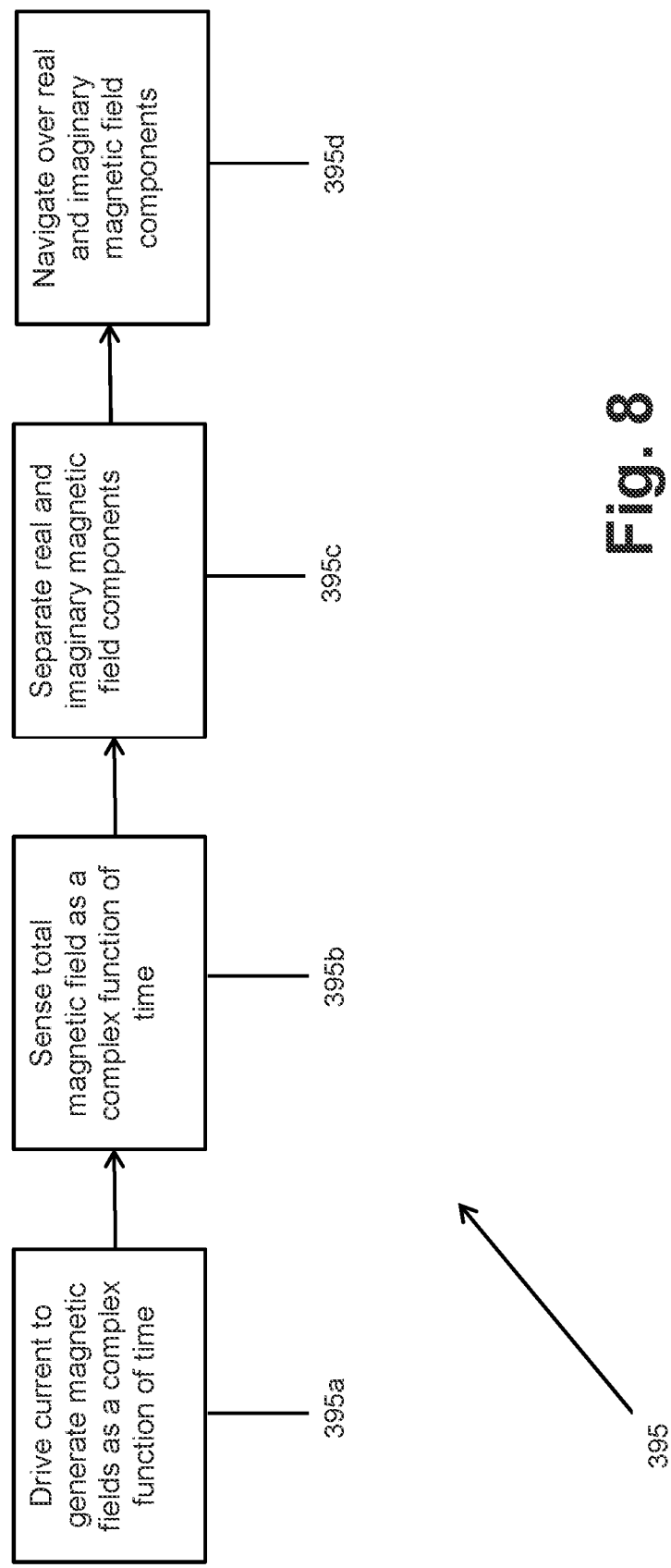
FIG. 8 is a flowchart including steps for navigating an instrument.

With reference to FIG. 8, a flowchart 395 is illustrated. The flowchart 395 may be incorporated in an algorithm that includes instructions that may be stored on a storage or memory system, such as a memory system of the navigation system 10, as discussed further herein. The instructions may be executed by the navigation processor 76 or other appropriate processor. The flowchart 395 may allow for determining or navigating based upon the fields formed by the TCA 30 and fields generated due to the eddy currents in the conductive member 90.

In the flowchart 395, in a first block 395*a* a drive current is used to generate a magnetic field as a complex function of time by driving current into the coils of the TCA 30. Each of the coils of the TCA 30 may be driven in various multiplexing manners to allow distinguishing between each field generated by each coil. Multiplexing may include frequency multiplexing, time multiplexing, code multiplexing, and/or combinations of multiplexing. After driving current to generate the field with the TCA 30, a tracking device, such as the tracking device 52 of the instrument 50 may sense the total magnetic field as a complex function of time in block 395*b*.

The sensed total magnetic field may then be transferred to a processor system, for example the navigation processor 76, as discussed above, which may include or access instructions to separate real and imaginary field components sensed by the tracking device in block 395*b*. It is understood that any appropriate processor system or processor specifically designed or a general purpose processor executing code may be used for separation of the real and imaginary components of the magnetic field. The separation of real and imaginary magnetic field components in block 395*c* may be based upon generally known computations, as is generally understood by one skilled in the art. The separation of the real and imaginary magnetic field components, however, allows for the sensed total magnetic field to be analyzed in further detail to allow for a greater accuracy of tracking the tracking device 52. Further, by accounting for the real and imaginary magnetic field components, the field generated due to the eddy currents in the conductive member 90 may be used to provide additional field diversity and tracking information for navigation of the instrument 50.

Accordingly, navigation of the instrument 50 by sensing the field with the tracking device 52 may allow for navigation over the real and imaginary magnetic field components in block 395*d*. As discussed above, and further herein, the navigation system 10 may be used to navigate the location of the instrument 50 by sensing the field generated by the localizer 20 which may include fields generated by the TCA 30 and fields generated due to eddy currents in the conductive member 90. Moreover, the eddy currents generated in the conductive member 90 may be based upon the shape, size, and location of the magnetically permeable members 82 relative to the conductive member 90. Accordingly, as discussed above, the shape and position of the coils of the TCA 30 and of the field shaping components 80 may generate a field that allows for navigation of the instrument 50.

With reference to FIG. 9, the localizer 20 may be used in the navigation system 10, as discussed above. The localizer 20 may be positioned relative to a subject, such as a patient 400, while a user 402 operates or moves the instrument 50 having the tracking device 52 associated therewith. The DRF 54 may be connected to the subject 400. The subject 400 may be positioned near or adjacent the localizer 20. The localizer 20 may be held and supported on a support 384, such as an operating room table. The navigation system 10 may also include a second localizer, such as an optical localizer 420.

Tracking information, including magnetic fields sensed with the tracking devices 52, 54 may be delivered via a communication system, such as a coil array and tracking device controller 430 to the navigation processor 76. Navigation processor 76 may be a part of a work station or computer system 434 that includes a display 436 to display an image 440. Further, a tracked location of the instrument 50 may be illustrated as an icon 442 relative to the image 440. Various other memory and processing systems may also be provided such as a memory system 446 in communication with the navigation processor 76 and an imaging processing unit 448. The image processing unit 448 may be incorporated into imaging system 450, such as the O-arm® imaging system, as discussed above. The imaging system 450 may be a x-ray imaging system including a x-ray source 452 and a detector 454 that are moveable within a gantry 460. The imaging system 450 may also be tracked with a tracking device 464.

Information from all of the tracking devices may be communicated to the navigation processors 76 for determining a location of the tracked portions relative to each other and/or for localizing the instrument 50 relative to the image 440. The imaging system 450 may be used to acquire image data to generate or produce the image 440 of the subject 400. It is understood, however, that other appropriate imaging systems may also be used. The coil array controller 430 may be used to operate and power the TCA 30 and the localizer 20, as discussed above.

The localizer 20, as discussed above, may include a various components including the TCA 30 that includes one or more coils positioned relative to one another and other components, such as the field shaping assembly 80. As discussed above, the field shaping assembly 80 may be positioned within a holding structure and include various other portions such as one or more cover portions 100, 104 and holding portions such as the structural or holding component 110. As illustrated above, the localizer 20 includes the TCA 30 positioned on the structural component or positioner 110 relative to the field shaping assembly 80. The field shaping assembly 80, as discussed above and illustrated in FIG. 1, includes a plurality of or portions such as the magnetic permeable member 82 positioned relative to a coil group, such as the coil group 34. A plurality of the magnetic permeable members 82 are positioned spaced apart from one another relative to the single conductive member 90. Accordingly the localizer 20 may include a plurality of coil groups in the TCA 30 that are positioned relative to a plurality of the magnetically permeable members 82 all positioned relative to the single or one conductive member 90. It is understood, according to various embodiments, that the localizer 20 may include different configurations including the coil groups in the TCA 30, the magnetic permeable members or single member 82, and the conductive member 90.

Figure 10A:
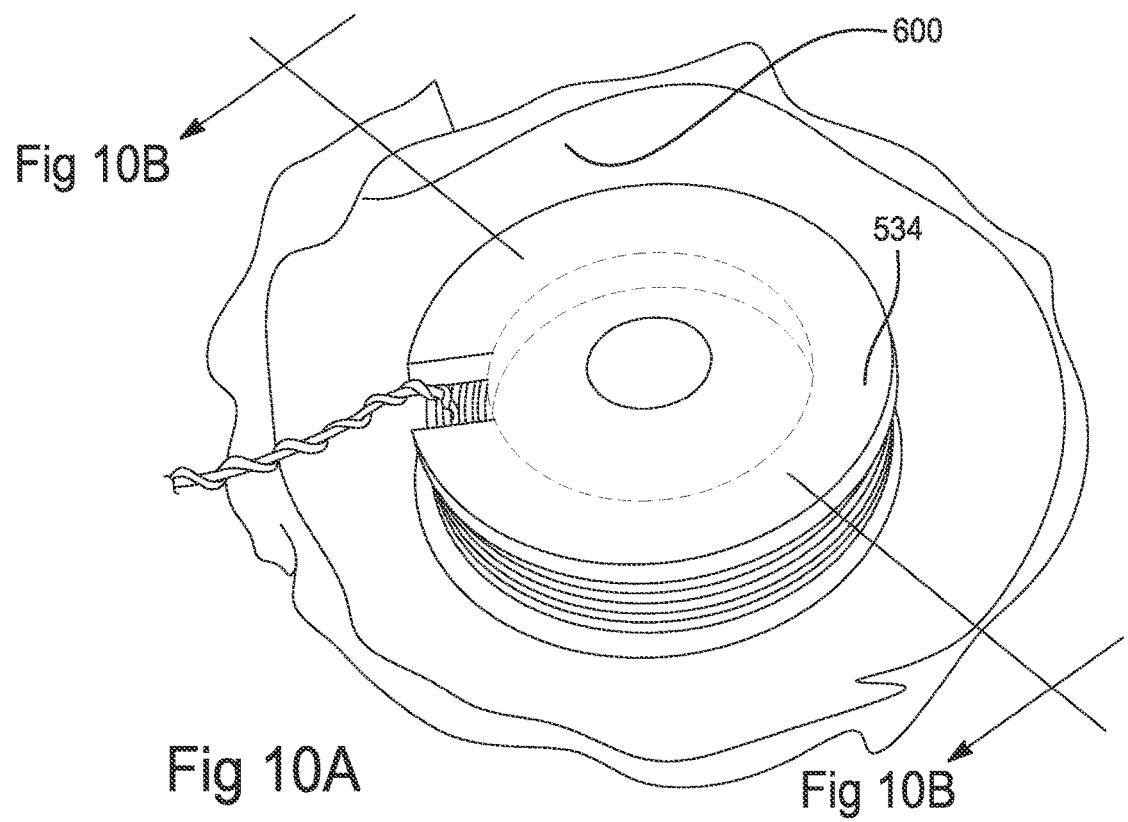
FIG. 10A illustrates a field shaping assembly, according to various embodiments.
Figure 10B:
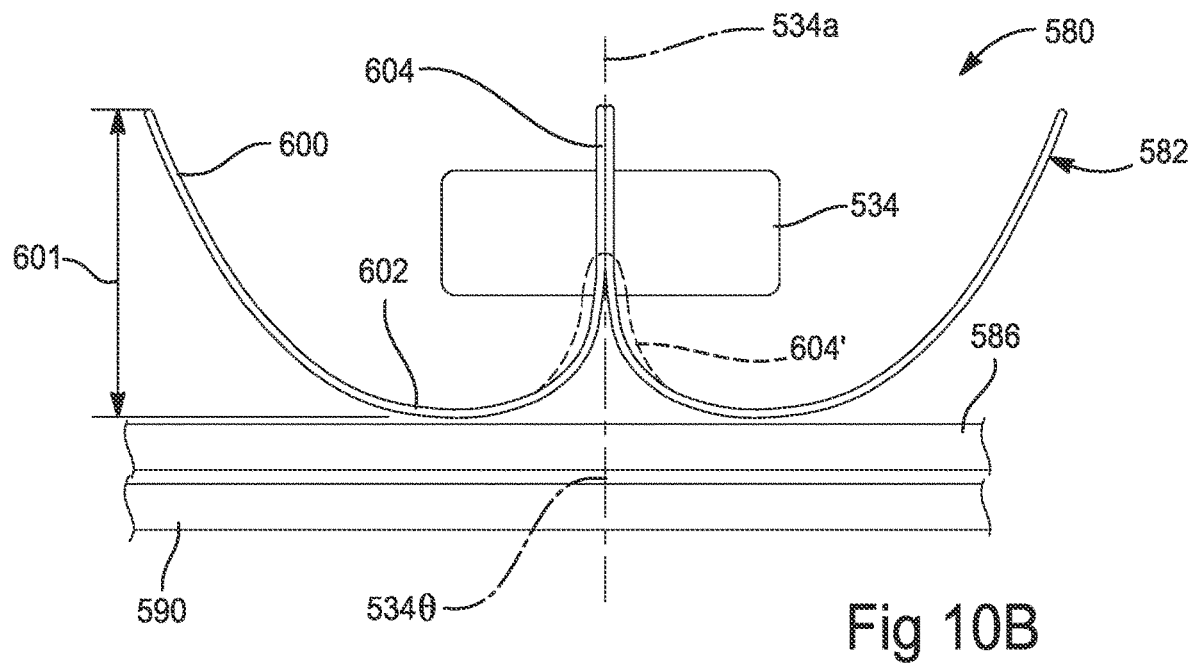
FIG. 10B is a cross-section of FIG. 10A.

According to various embodiments, with reference to FIG. 10A and FIG. 10B, the localizer 20, or other appropriate localizer, including those discussed further herein may include components or portions similar to the localizer 20 illustrated in FIG. 1. According to various embodiments, however, the localizer may include different shapes and/or configurations of the TCA 30, and/or the field shaping assembly 80. For example, the field shaping assembly 80 may include a coil or coil group that may include one or more coils, such as a coil 534. It is understood, that the discussion here of the coil 534 may refer to a plurality of coils, such as a plurality of coils in the coil groups, such as the coil group 34, discussed above. Accordingly, the discussion of the coil 534 as a single coil is merely exemplary and the coil 534 and the related assembly may be repeated and selectively shaped, similar to the coils of the coil groups discussed above, to generate a selectively shaped (e.g. diverse) field that includes a selected or appropriate diversity, such as that discussed above.

With continuing reference to FIGS. 10A and 10B, the coil 534 may be positioned within a cup or well field shaping assembly 580. The field shaping assembly 580 may include a conductive member 590 and one or more spacer member portions 586, as discussed above. It is understood that the spacer 586, however, may be optional and is not necessary between the conductive member 590 and a well or cup magnetic permeable member or layer 582. The conductive member 590 may be formed of materials, including those discussed above. Further, the magnetic permeable member 582 may also be formed of the similar materials as discussed above. THE cupped shape magnetic permeable member may be provided to shape and direct the transmitted field form the coil 534, such as away from the coil 534, but within the outer wall 600.

The cupped magnetic permeable member 582 may include various portions or assemblies, such as a wall or upturned sidewall 600. The upturned sidewall may extend from a bottom wall 602 over which the coil 534 is positioned. The sidewall 600 may be positioned or formed to surround the coil 534. In addition to the sidewall 600 and the bottom wall 602, a punt or central wall or extension 604 may also extend from the bottom wall 602 up to and/or through the coil 534. As specifically illustrated in FIG. 10A, the punt wall 604 extends through the coil 534. It may be possible that the punt wall 604 acts as a core for the coil 534. It is understood, however, that the punt wall portion 604 may only extend a portion through or into the coil 534 as illustrated in Fanta 604'.

The magnetic permeable member 582 may interact with a field transmitted or generated by the coil 534 in a manner similar to that discussed above. Given the shape and/or position of the magnetic permeable member 582 the field or field lines formed by the coil 534 may be positioned or shaped relative to the conductive member 590.

In addition, the coil 534 may be positioned substantially perpendicular to the conductive member 590. In other words, a central axis 534a or axis around which the coil 534 is wound, may be formed at an angle or positioned at an angle 534θ relative to a surface of the conductive member 590. In various embodiments, the axis 534a may be substantially perpendicular such as the angle 534θ is 90 degrees or may be a non-90 degree angle. For example, the angle 534θ may be about 40 degrees to about 150 degrees. As discussed above, positioning the coil 534 within the magnetic permeable member 582 may position or move the field formed by the coil 534 relative to the conductive member. It is further understood that the coil 534 and the magnetic permeable member 582 may be formed as a unit such that the punt wall 604 may be positioned along the axis 534a and may also be moved at the selected angle or position of the selected angle 534θ relative to the conductive member 590.

With continuing reference to FIG. 10A and additional reference to FIGS. 10C and 10D the cupped or well-shaped magnetic permeable member 582 may be selectively sized and/or shaped relative to the coil 534. As illustrated in FIG. 10C, the magnetic permeable cup 582 includes a cup 582' that includes a side wall 600' that has a height 601' from a bottom surface or plane, such as the bottom wall 602'. The height 601' may also be relative to a surface of the conductive member 590 and from the bottom wall 602' is merely exemplary. However, the height 601' may be less than a height 601 of the magnetic permeable 582, illustrated in FIG. 10A. Further, the magnetic permeable member 582', according to various embodiments, does not and need not include the punt wall 604. It is further understood that the spacer 586, according to various embodiments, may include an air gap or space between the magnetic permeable member 582' or magnetic permeable member 582 or 82, and the respective conductive member.

The coil 534 may be positioned relative to the magnetic permeable member 582' in any appropriate manner, such as with a spacer 605 which may be formed of a substantially inert material (e.g. non-conductive and/or non-magnetically interfering or distorting such as non-conductive cloth or other textile material or polymer material). The coil 534, therefore, may be positioned relative to the magnetic permeable member 582' to form a field relative to the conductive member 590, as discussed above. The shape and position of the magnetic permeable member 582', however, may influence or shape a field formed or transmitted by the coil 534. Again, the spacer 586 may be selected with the position between the magnetic permeable member 582' and the conductive member 590 or may be selectively not positioned. Further, the transmitted field from the coil 534 may induce a current in the conductive member 590 which then generates an induced field, as discussed above. The induced field may be diverse or have diverse components relative to the transmitted field. Shaping and/or angling the magnetic permeable member 582' relative to the conductive member 590 may further create the diverse field.

With continuing reference to FIG. 10A and additional reference to 10D, a magnetic permeable member 582" is illustrated. The magnetic permeable member 582" includes a sidewall 602" that has a height 601" relative to a bottom wall 602". Again the height 601" may be different, such as less than, the height 601' and/or the height 601. In various embodiments, the height 601" may be such that the sidewall 602" includes an upper or terminal surface or edge 603 that is below a portion, such as any portion, including at least a top portion, of the coil 534. Accordingly, it is understood that the magnetic permeable member 582 may be shaped relative to the coil 534, or any appropriate coil for forming or shaping the localizer 20 to shape a selected field.

In addition to, or alternatively to the above described embodiments of the TCA 30 and the various coils and coil groups thereof, the localizer 20 may include embodiments as discussed and illustrated herein. It is understood that while an exemplary coil or coil group may be discussed, a plurality of each may be included in a single localizer, such as the localizer 20 discussed above.

Turning reference to FIG. 11A, FIG. 11B, and FIG. 11C field shaping components, according to various embodiments, are illustrated. The field shaping components may include a substantially circular geometry, including a field shaping component or assembly 680 as illustrated in FIG. 11A. As illustrated in FIG. 11B a field shaping component or assembly 780 may include an elongated or oval shape, as discussed further herein. Further, as illustrated in FIG. 11C a field shaping component or assembly 880 that may include various shapes, such as a rounded triangle, rounded corner triangle, or other complex shapes. Accordingly, the field shaping component or assembly, such as the circular field shaping component 680, the oval field shaping component 780, or the complex shape field shaping component 880 may be included with the localizer 20, or any appropriate localizer. As discussed above, each field shaping component or assembly may have a coil positioned relative thereto.

With additional reference to FIG. 11A, the field shaping component 680 may have positioned relative thereto a coil such as a coil 634. The coil 634 may be positioned at a center 690 of the field shaping component 680. It is understood, however, that a central axis (e.g. an axis around which the coil 634 is wound) may be positioned off center or away from the center 690 of the field shaping component. Nevertheless the field shaping component 680 may include a magnetic permeable member or portion 682 that has a radius 682r. The field shaping component 680 may also include additional portions or members, such as those discussed above, including a conductive layer portion 690. As discussed above one or more spacer portions may be positioned between the magnetic permeable member 682 and the conductive member 690. The field shaping component 680, according to various embodiments including those also as discussed above, may further include a second or auxiliary magnetic permeable member or portion 696. Accordingly, the field shaping component 680 may include the conductive member 690 positioned between the first magnetic permeable member 682 and the second magnetic permeable member 696.

Thus, the first magnetic permeable member 682 and the second magnetic permeable member 696 are on opposite or opposed sides of the conductive member 690. It is understood, that various shapes of field shaping components may also include this construction or arrangement.

In various embodiments, the magnetic permeable member positioned on a side of a conductive member away from a coil transmitting a field may assist in absorbing additional field from the coil that would extend beyond the conductive member. For example, the second magnetic permeable member 696 may absorb field form the coil 634 that extends beyond the conductive member 690. Therefore, an interfering object or object on a side of the conductive member away from the coil 634 is less likely or will not influence or have induced therein a current. It is understood, the second or auxiliary magnetic permeable member of the field shaping assembly according to various embodiments may produce the same or similar effect.

Further each of the members or components may be positioned relative to one another. For example, the conductive member 690 may include an area or region 690a that extends beyond an outer edge of the first magnetic permeable member 682 and the second magnetic permeable member 696 includes an area or region 696a that extends beyond an edge of the conductive member 690. It is understood that the second magnetic permeable member 696 may be selected to be optional and need not be required or included in the field shaping component 680. Further, according to various embodiments, a second magnetic permeable member may be included in any appropriate field shaping component assembly, including the field shaping assembly 80 (as illustrated in FIG. 1) and/or other field shaping assemblies including the field shaping assembly 580 discussed above.

Turning reference to FIG. 11B, the field shaping component 780 may include a first magnetic permeable member 782 positioned over or relative to a conductive member or component 790 and a second magnetic permeable member 796. As discussed above each of the respective members, such as the conductive member 790 and the second magnetic permeable member 796 may have an edge that extends beyond an edge of the member or portion above it. Accordingly the field shaping assembly 780 may again include the first magnetic permeable member 782 and the second magnetic permeable member 796 with the conductive member 790 therebetween. It is further understood, however, that the second magnetic permeable member 796 may be optional.

The field shaping component 780 may include or have positioned relative thereto a coil 734. A center of the coil 734c may be positioned or offset from a center or point 782c of the first magnetic permeable member 782. The shape of the first magnetic permeable member 782 may include a first distance or radius 782r' and a second distance or radius 782r". The two radii 782r', 782r" may be different to provide or give a selected shape to the magnetic permeable member 782. Further the coil 734 may be positioned that a center or central axis 784c may be positioned at the point 782c. Positioning the coil 734 relative to or at a different location on the magnetic permeable member 782 may be selected to achieve a selected shape of a field formed by the coil 734, as discussed above, to include or create a selected field diversity.

Turning reference to FIG. 11C, the field shaping assembly 880 may include a first magnetic permeable member 882, a conductive member 890, and a second magnetic permeable member 896. Again, the second magnetic permeable member 896 may be optional, but if selected the conductive member 890 may be positioned between the first magnetic permeable member 882 and the second magnetic permeable member 896. The shape of the first magnetic permeable member 882 may be a selected shape such as a complex shape including a generally triangular portion 882t and a rectangular portion 882r. The first magnetic permeable member 882 may be formed as a single piece but including the selected shape as illustrated in FIG. 11C. It is understood, however, as discussed further herein, that the field shaping assembly may have an appropriate shape to achieve a selected diversity. Accordingly, a coil 834 may be positioned such that a center or central axis 834c is positioned in one of the regions of the magnetic permeable member 882, such as in the triangular 882t. Further, the connective member 890 may extend beyond an external edge or parameter of the first magnetic permeable member 882 and the second permeable member 896 may extend beyond a parameter of the connective member 890.

As illustrated in FIGS. 11A, FIG. 11B, and FIG. 11C the respective coils 634, 734, 834 include substantially round perimeters or cylindrical shapes. Accordingly distance from the respective centers to the outer perimeters of the respective coil 634, 734, 834 may be substantially uniform around the outer perimeters of the coil. It is understood, however, that the coils may include non-circular or cylindrical shapes, including oval or asymmetrical shapes, as discussed above. Further, as also illustrated in FIGS. 11B and 11C and as exemplary described and discussed relative to FIG. 11A the respective coils may be positioned at asymmetrical or non-central locations of the respective field shaping assemblies.

With reference to FIG. 11A, FIG. 11B, and FIG. 11C a field shaping component may include a single coil positioned relative thereto. In various embodiments, however, a plurality of coils may be positioned relative to the respective field shaping assemblies. Also, the plurality of coils may be placed asymmetrically, such as not equidistant apart or from edges, of the respective field shaping assemblies.

As illustrated in FIG. 12A selected field shaping assemblies may include a plurality of coil positioned relative thereto, as discussed above as illustrated in FIG. 1. With additional reference to FIG. 12A a field shaping assembly 980 is illustrated. The field shaping assembly 980 may include a first magnetic permeable member 982 and a conductive member 980. Again, the field shaping assembly 980 may include an optional second magnetic permeable member 996 wherein the conductive member 990 is positioned between the first magnetic permeable member 982 and the second magnetic permeable member 996. The field shaping assembly 980 may have a selected shape, such as a substantially triangular shape. Further a coil group may include a first coil 934a, a second coil 934b, and the third coil 934c. Each of the coils 934a, 934b, and 934c may be positioned away from a center and/or near a corner of the triangle. Each of the coils 934a, 934b, 934c may have a respective center and may be substantially round or cylindrical shaped. The coils, however, may generate a field that is substantially diverse due to the field shaping assembly 980, as discussed above.

Turning reference to FIG. 12B a field shaping assembly 1080 is illustrated. The field shaping assembly 1080 may be substantially rectangular and include a first magnetic permeable member 1082 and a conductive member 1090. Again an optional second magnetic permeable member 1096 may be positioned such that the conductive member 1090 is between the first magnetic permeable member 1082 and the second magnetic permeable member 1096. As discussed above each of the respective members 1090 and second permeable member 1096 may have an outer parameter that extends a selected distance or area beyond the adjacent or next layer. Further, selected spacers may be positioned between each of the respective layers 1082, 1090, 1096 as discussed above.

Positioned relative to the first magnetic permeable member 1082 may be a coil group including a first coil 1034a, 1034b, and 1034c. Each of the coils may be elongated or ellipsis or oval in shape rather than round. Accordingly, each of the coils 1034a, 1034b, and 1034c may generate or transmit a field relative to the field shaping assembly 1080 that is different than a field generated by a cylindrical or round coil. Again the respective shape of the coils and the field shaping assembly 1080 may affect or generate a selectively diverse field as discussed above.

As discussed and illustrated in FIG. 11A, FIG. 11B, FIG. 11C, FIG. 12A, FIG. 12B, and in various embodiments as discussed above, different portions of the field shaping assemblies may be substantially independent of other field shaping assembly portions. In various embodiments, as illustrated in FIG. 1, a plurality of coil groups may be positioned relative to a plurality of separated magnetic permeable members 82 that are all positioned on a single or unitary conductive member 90 of the field shaping assembly 80. It is understood that alternative embodiments and/or additional embodiments may be used either alone or in combination with the field shaping assembly 80 or as otherwise understood by one skilled in the art.

Turning reference to FIG. 13, a field shaping assembly 1180 is illustrated. The field shaping assembly 1180 includes various portions such as a first magnetic permeable member 1182, a conductive member 1190, and a second magnetic permeable member 1196. The first magnetic permeable member 1182 may be provided as one or more members that are formed as substantially single units or members that are spaced apart from one another, such as a first spacing 1200 and a second spacing 1204, but positioned over or on the connective member 1190. Accordingly, as illustrated in FIG. 13 the conductive member 1190 may have an external edge 1206 that extends beyond an external edge of any one of the member 1182, which may include four magnetic permeable members 1182a, 1182b, 1182c, or 1182d. The conductive member 1190 may be provided or formed as a single piece. As a single piece the conductive member 1190 is conductive throughout its area.

The first magnetic permeable members 1182 positioned on or over the conductive member 1190 may be similar to the embodiment illustrated in FIG. 1. It is understood, however, that various spacers may also be positioned between the magnetic permeable members 1182 and the conductive member 1190. As illustrated in FIG. 13, however, an alternative second magnetic permeable member 1196 may be positioned on an opposite side of the conductive member 1190 from the first magnetic permeable members 1182. An external or outer parameter 1210 of the second magnetic permeable member 1196 may extend beyond the outer parameter 1206 of the conductive member 1190. It is understood, however, that the second magnetic permeable member 1196 may be provided as a single member that extends as a single member or formed as a single member within the parameter 1210 of the magnetic permeable member 1196.

It is further understood, however, that a second magnetic permeable member 1196 may be optional and is not required. Further it is understood that the first magnetic permeable members 1182 may be provided in any appropriate number and four is merely exemplary. Further the field shaping assembly 1180 may be provided as a portion of the localizer 20, as discussed above, including the TCA 30 and/or a TCA 1130 as illustrated in FIG. 13. The TCA 1130 may include a plurality of coil groups such as a first coil group 1134, a second coil group 1136, a third coil group 1138, and a fourth coil group 1140. Each of the coil groups may include a selected number of coils, such as three coils illustrated in FIG. 13, including the three coils 1134a, 1134b, and 1134c of the first coil group 1134; a first coil 1136a, a second coil 1136b, and a third coil 1136c of the second coil group 1136; a first coil 1138a, a second coil 1138b, and a third coil 1138c of the third coil group 1138; and a first coil 1140a, a second coil 1140b, and a third coil 1140c of the fourth coil group 1140. If less than four of the magnetic permeable members 1182 are provided, less coil groups may also be provided. Nevertheless, each of the coils of the respective coil groups 1134-1140 may generate a field relative to the field shaping assembly 1180.

The field shaping assembly 1180, however, in combination with the TCA 1130 may generate the selectively diverse field as discussed above. The field shaping assembly 1180 may include various features such as shapes of the first conductive member 1182, including those discussed above, or any appropriate shape. Further, the field diversity may be achieved by positioning the coils of the TCA 1130 relative to the first magnetic permeable members 1182 in a selected or appropriate manner to achieve the selected diversity. For example, asymmetrically placing the coils relative to the first magnetic permeable members 1182 may achieve the appropriate or selected diversity of the field. Also, as discussed above, a portion of the transmitted field that extends beyond the first magnetic permeable members 1182 may induce a current in the conductive member 1190, which, in turn, will generate an induced field.

Accordingly, although rectangular members are illustrated in FIG. 13, it is understood that the first conductive members 1182 may be circular, trapezoidal, or other appropriate shape even if placed on the conductive member 1190 that is substantially rectangular. Moreover, the conductive member 1190 may be provided as individual separated members such as the conductive member 1190 not being provided as a single unitary member, but as at least two members that are positioned between the first magnetic permeable members 1182 and the first magnetic permeable members 1196 with the one or more conductive members 1190 therebetween. It is further understood, however, that the second magnetic permeable member 1196 is optional and therefore two or more conductive members 1190 may be positioned relative to the first magnetic permeable members 1182 to form the field shaping assembly 1180 with the TCA 1130.

Further the selected coils of the coil groups 1134-1140 of the TCA 1130 may be selectively shaped, such as oval, round, cylindrical, or other appropriate shape relative to selected field shaping members of the field shaping assembly 1180. It is further understood that the TCA 1130 may include the connections and controls, as discussed above, for driving and otherwise operating a localizer 20. The coils of the TCA 1130 are shown relative to the field shaping assembly 1180 as merely exemplary and being shown without the other portions of the localizer assembly.

Accordingly, as discussed above, the TCA according to various embodiments, including those discussed above in combination and/or alternatively to one another, may be used to generate a field. A field shaping assembly, also according to various embodiments including those discussed above as alternatives or in addition to one another, may be used to shape the field selectively. The shaped field achieves a selected diversity, as also discussed above, to allow for tracking of a selected sensor within a navigation domain or volume. The diversity provides for or allows for a plurality of vectors that are orthogonal or substantially orthogonal to one another to assist in increased accuracy and/or speed in determining a location of the tracking device. In various embodiments, a transmitted field may be or is diverse relative to an induced field (i.e. generated from an induced current in a conductive member). Accordingly, the tracking coil or other sensor that has been tracking space with the navigation domain may be resolved substantially precisely or accurately in three-dimensional space including an X,Y,Z position and orientation, including at least one of yaw, pitch, or roll.

The field shaping assembly, such as the field shaping assembly 80, or according to any appropriate embodiment including those discussed above, may include the magnetic permeable members of the materials discussed above and the conductive member of the materials discussed above. Accordingly, various embodiments are discussed that may be combined or provided as alternatives to one another. Nevertheless, the field shaping assemblies, as discussed herein, may operate to substantially reduce or eliminate distortion or interference that may be introduced by a conductive member other than the field shaping assembly. Therefore, tracking of the tracking device in the navigational domain may be substantially immune to various members or materials that may affect the field produced by the TCA.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system having a localizer, comprising:
   a transmitting coil array operable to generate a transmitted magnetic field, the transmitting coil array including a first coil positioned along a first plane, a second coil positioned along a second plane, and a third coil positioned along a third plane;
   a field shaping assembly, comprising:
   a conductive member having a first surface extending along a fourth plane with a first surface area;
   a first magnetic permeable member having a second surface with a second surface area; and
   a structural component having a coil holding region, the coil holding region having,
   a first coil pocket having a first bottom surface defining the first plane and a first raised outer wall configured to hold the first coil relative to the first plane,
   a second coil pocket having a second bottom surface defining the second plane and a second raised outer wall configured to hold the second coil relative to the second plane, and
   a third coil pocket having a third bottom surface defining the third plane and a third raised outer wall configured to hold the third coil relative to the third plane;
   wherein the field shaping assembly and the transmitting coil array cooperate to generate a field;

wherein the first plane, the second plane, and the third plane are each at a non-zero angle relative to the fourth plane.

2. The system of claim 1, wherein the transmitted magnetic field induces a current in the conductive member to generate an induced magnetic field;
wherein the current flows around the first magnetic permeable member in the conductive member.

3. The system of claim 2, wherein a first vector of a first component of the transmitted magnetic field is diverse relative to a second vector of a second component of the induced magnetic field.

4. The system of claim 3, wherein the first component and the second component are time.

5. The system of claim 1, wherein the field shaping assembly further comprises:
a second magnetic permeable member having a third surface with a third surface area;
wherein conductive member is positioned between the first magnetic permeable member and second magnetic permeable member;
wherein the third surface area is greater than the first surface area and the first surface area is greater than the second surface area.

6. The system of claim 1, wherein the field shaping assembly further comprises:
a second magnetic permeable member having a third surface with a third surface area;
wherein the first surface area is greater than a combined surface area of the second surface area and the third surface area;
wherein the first magnetic permeable member and second magnetic permeable member are both positioned on a single side of the conductive member.

7. The system of claim 6, wherein the first magnetic permeable member and second magnetic permeable member are spaced apart on the single side of the conductive member.

8. The system of claim 3, further comprising:
a tracking device configured to sense the transmitted field and the induced field; and
a processor configured to execute instructions to determine a location of the tracking device based on the sensed transmitted field and the induced field.

9. The system of claim 8, wherein the diversity of the first vector and the second vector allow for navigation of the tracking device in a navigation volume defined by at least a portion of the transmitted field and the induced field.

10. The system of claim 1, wherein the first coil is flat relative to at least one of the first magnetic permeable member or a second magnetic permeable member.

11. The system of claim 10, wherein the first coil is configured to induce a current in the conductive member.

12. The system of claim 11, wherein the induced current is around the at least one of the first magnetic permeable member or a second magnetic permeable member in the conductive member.

13. The system of claim 1, further comprising:
a processor system configured to receive a signal from a tracking device based on the sensed field to determine a location of the tracking device within a navigation volume.

14. The system of claim 13, further comprising:
a display device to display the determined location of the tracking device.

15. The system of claim 1, wherein the first coil, the second coil, and the third coil, are each spaced apart from one another and each have a separate center.

16. The system of claim 15, where each of the first coil, the second coil, and the third coil are each formed as an ellipse.

17. The system of claim 15, wherein the first coil, the second coil, and the third coil are spaced apart from one another around a center at about 120° apart from one another.

18. The system of claim 1, wherein the first coil pocket includes a projection extending from the first bottom surface, wherein the first projection is configured to pass through the first coil, where the first coil is positioned between the first projection and the first raised outer wall.

19. The system of claim 18, wherein the first coil is formed as an ellipse having a major axis and a minor axis and a central portion, wherein the projection is received within the central portion of the first coil.

* * * * *